United States Patent [19]
Takahashi

[11] Patent Number: 5,689,365
[45] Date of Patent: Nov. 18, 1997

[54] STEREOSCOPIC-VISION ENDOSCOPE

[75] Inventor: Susumu Takahashi, Iruma, Japan

[73] Assignee: Olympus Optical Co., Ltd, Tokyo, Japan

[21] Appl. No.: 526,103

[22] Filed: Sep. 11, 1995

[30] Foreign Application Priority Data

Sep. 13, 1994 [JP] Japan .................. 6-219028

[51] Int. Cl.⁶ .......................... G02B 21/36; G02B 21/20; G02B 21/22; G02B 21/00
[52] U.S. Cl. .................. 359/362; 359/363; 359/375; 359/376; 359/378; 359/381; 359/384; 359/462; 359/656
[58] Field of Search ........................ 359/362, 363, 359/376, 377, 381, 384, 462, 466, 472, 781, 783, 744, 656, 657, 658, 659, 660, 661, 375, 378; 600/111, 112; 348/45, 68

[56] References Cited

U.S. PATENT DOCUMENTS 4,905,082  2/1990  Nishigaki et al. ................ 358/98
5,191,203  3/1993  McKinley ........................ 250/208.1

*Primary Examiner*—Paul M. Dierzynski
*Assistant Examiner*—Mohammad Y. Sikder
*Attorney, Agent, or Firm*—Armstrong, Westerman, Hattori, McLeland & Naughton

[57] ABSTRACT

A stereoscopic-vision endoscope having an objective optical system consisting of a front optical system having a single optical axis including a field conversion optical system, and a rear optical system including optical systems that have a plurality of optical axes. A light beam is received from the front optical system so as to form images on the optical axes, and thus form a plurality of images. The front and rear optical systems can be turned relative to each other. Thus, a magnitude of parallax permitting a sufficient sense of three-dimensionality can be provided, and the postures of images can be corrected responsively to a change in direction of view resulting from the rotation of an insertional part.

16 Claims, 25 Drawing Sheets

RELATED ART

RELATED ART

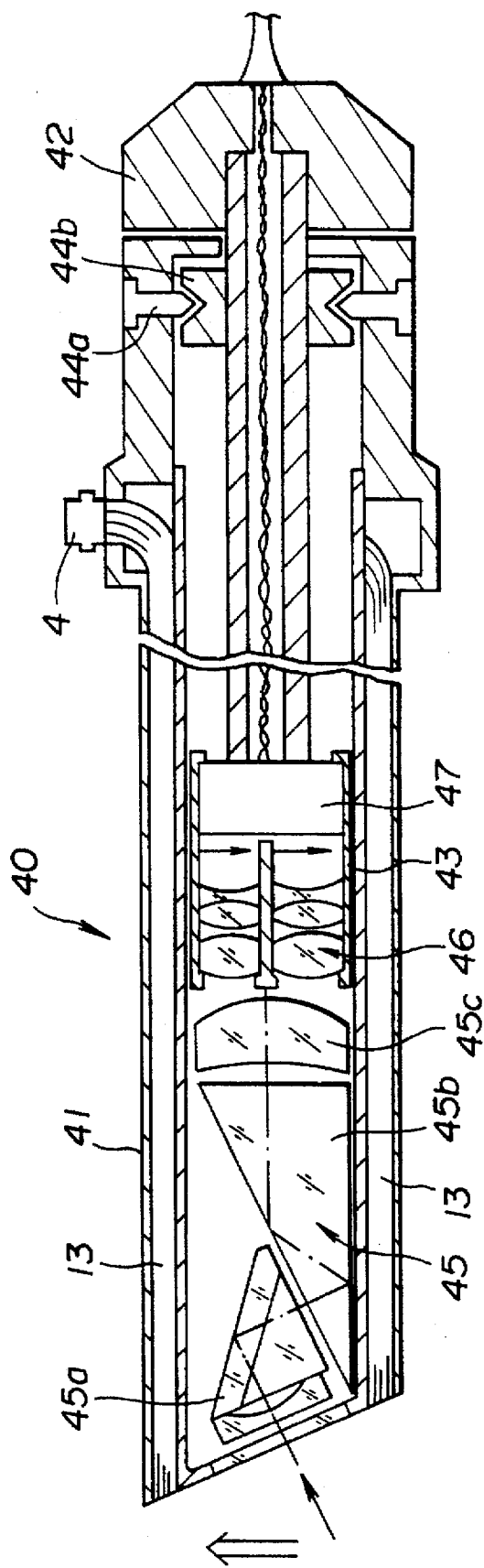

STEREOSCOPIC-VISION ENDOSCOPE

BACKGROUND OF THE INVENTION

1. Field of the Invention

The present invention relates to a stereoscopic-vision endoscope enabling three-dimensional viewing of a region to be observed.

2. Description of the Related Art

An endoscope whose elongated insertional part is inserted into a body cavity in order to view an invisible region to be examined has been widely adopted.

Taking surgery for instance, laparotomy has commonly been conducted in the past. With the evolution of surgical procedures, trans-endoscopic surgery has come to serve as a substitute for laparotomy. That is to say, a small orifice is formed in the abdomen of a human being, and an endoscope or therapeutic instrument is inserted into the abdominal cavity through the orifice for the purpose of viewing or surgery.

In such a trans-endoscopic surgery, a TV camera is attached to an eyepiece unit of a rigid endoscope so that treatment can be conducted with the viewing of an object region through a monitor. As far as an ordinary endoscope is concerned, a region to be viewed can be seen as a mere plane devoid of depth perception. It is therefore difficult to observe fine irregularities on the surfaces of walls of a body cavity or the surface of an organ. Because of lack of depth information, diagnosis or various treatments to be performed through endoscopic viewing cannot be easily achieved. This makes the treatments time-consuming, resulting in prolonged operation time.

In an effort to solve this problem, stereoscopic-vision endoscopes enabling stereoscopic viewing of regions have been developed in recent years. In such a stereoscopic-vision endoscope, an optical system having a plurality of optical axes is used, and a viewing optical system is situated so that parallax will occur relative to the optical system.

The stereoscopic-vision endoscope has an elongated insertional part to be inserted into a body cavity. An optical system having a plurality of optical axes and forming right and left images causing parallax is mounted in the insertional part. The right and left images are picked up by imaging means and displayed by a three-dimensional image display system, whereby viewers can discern a region to be viewed three-dimensionally.

The three-dimensional image display system is realized by wearing glasses with shutters, which are opened and closed responsively to right and left images that are represented by video signals sent from a camera control unit and displayed time-sequentially in an alternating fashion on a speed-multiplication display type TV monitor via a scan converter, so as to view the right and left images. Herein, the glasses allow a viewer's right and left eyes to see corresponding images alone. In another proposed three-dimensional image display system, a polarizer such as a polarization filter is attached to a monitor in order to modulate right and left images to be displayed on the monitor. This results in polarized light components which are mutually orthogonal. A viewer wears polarization glasses which transmit the resultant light components corresponding to his/her right and left eyes, thus resulting in stereoscopic vision. According to another proposed three-dimensional image display system, a compact monitor is attached to each of the right and left sides of glasses or the like to be mounted on a viewer's head, and right and left images are displayed on the monitors for stereoscopic viewing.

Since an endoscope system with a stereoscopic-vision endoscope having the aforesaid configuration has been developed, any region to be viewed can be discerned three-dimensionally. A larger amount of information concerning the inside of a body cavity such as depth information concerning a region to be viewed has come to be available. The region to be viewed can be discerned almost in the same manner as it is seen by the naked eye.

FIG. 1 shows an example of the structure of a conventional stereoscopic-vision endoscope. The conventional stereoscopic-vision endoscope 51 is an example of a skew-view rigid endoscope having a rigid insertional part. An imaging unit 54 including imaging devices 53 is united with the proximal end of the insertional part 52. Two optical systems 55 that are right and left independent optical systems are juxtaposed in order to form right and left images causing parallax required for stereoscopic visioning, and are incorporated in the insertional part 52. FIG. 1 shows only one of the optical systems. The two optical systems abut each other side-by-side. In the optical systems 55, systems of relay lenses 57 transmit images formed by systems of objective lenses 56 toward distal portions of the optical systems 55. The images are then projected on the right and left imaging devices 53. A light guide 58 connected to a light source unit is running along the outer circumferences of the optical systems 55 in the insertional part 52, whereby illumination light emanating from the light source unit is transmitted to the distal portions of the optical systems 55.

However, when the insertional part is rotated for better viewing during, for example, trans-endoscopic surgery, if a stereoscopic-vision endoscope having the conventional structure shown in FIG. 1 is used, the directions of gravity of picked-up images of a region to be viewed are inconsistent with the directions of gravity of images displayed on the monitor. The view is therefore indiscernible. It then becomes difficult to evaluate the object region and proceed a surgical procedure.

As shown in FIGS. 2A, 2B, 3A, and 3B, when the stereoscopic-vision endoscope having the conventional structure is used for skew viewing, if the optical systems 55 are, as shown in FIG. 2A, oriented vertically, the directions of gravity of images appearing on the monitor shown in FIG. 2B are consistent with the direction of gravity of a region to be viewed (indicated with an arrow). When the insertional part is, as shown in FIG. 3A, turned and the optical systems 55 are oriented sideways, picked-up images are tilted. The directions of gravity of images appearing on the monitor shown in FIG. 3B becomes inconsistent with the direction of gravity of the region to be viewed. The view is therefore indiscernible. The direction of gravity of the region to be viewed is not likely to be grasped from the view obtained through the monitor. A viewer may become confused. For surgical use, the endoscope is not user-friendly.

As far as a direct-view rigid endoscope that is not designed for stereoscopic visioning is concerned, a main unit of a rigid endoscope must first be positioned so that the external portions of light guide cables or the like will be arranged in a direction not interfering with the progress of surgery. A TV camera attached to an eyepiece unit is then turned, whereby the directions of gravity of images appearing on a monitor can be matched with the direction of gravity of a region to be viewed without a need for moving the main unit of the rigid endoscope. However, when it comes to the conventional stereoscopic-vision endoscope, because the two optical systems are juxtaposed, when the imaging means are turned relative to the optical systems, a light beam is obstructed to cause vignetting. It is theoretically impossible to turn the imaging unit relative to the main unit of the endoscope. As for the direct-view stereoscopic-vision endoscope, the directions of gravity of images appearing on the monitor can be matched with the direction of gravity of a region to be viewed by turning the entire endoscope. However, since the imaging unit cannot help but be turned together with the optical systems, the endoscope cannot be set up in a state ensuring smooth surgery. This brings surgery into confusion.

In an effort to solve the above problems, the present applicant has proposed a stereoscopic-vision endoscope, which is disclosed in Japanese Patent Laid-Open No. 6-59199 and shown in FIG. 4, so as to enable stereoscopic-vision skew viewing. According to the structure of the stereoscopic-vision endoscope 61, an optical system whose elements share the same optical axis is used to realize a system of objective lenses 62 and a system of relay lenses 63. A pupil dividing prism 64 is used to decompose an exit pupil formed by the optical system into right and left light beams, whereby stereoscopic-vision viewing is enabled. This structure is generally referred to as a pupil division type.

In a pupil division type stereoscopic-vision endoscope, a pupil dividing prism for decomposing an exit pupil formed by a system of relay lenses into right and left light beams, an image formation optical system for forming the right and left images, and imaging devices for picking up the right and left images are rotated as a united body about the optical axis shared by the system of objective lenses and system of relay lenses. In other words, an imaging unit 66 coupled to the proximal end of an insertional part 65 shown in FIG. 4 is rotated relative to the insertional part 65. Even for the optical system designed for skew viewing, the postures of images can be corrected responsively to the turn of the insertional part in a manner such that the direction of gravity of a view will remain constant.

According to the foregoing structure, even when a main unit-of a direct-view stereoscopic-vision endoscope including an insertional part is rotated and thus adjusted for ease of operation, the direction of gravity of a view can be corrected merely by rotating an imaging unit located at the proximal end of the main unit irrespective of the angular position of the main unit. Surgery will therefore not be in a confused state; operability can be maintained; and stereoscopic viewing can be reliably carried out.

U.S. Pat. No. 5,191,203 has disclosed a stereoscopic-vision endoscope having the structure shown in FIG. 5 in which an optical system 68 consisting of two optical systems is juxtaposed behind an optical system 67 having a single optical axis, pluralities of right and left light beams are extracted in order to project right and left images on a CCD array 69. However, no mention is made of skew viewing. No consideration is taken into the aforesaid correction of postures of images.

The aforesaid pupil division type stereoscopic-vision endoscope is capable of correcting postures of images of an object so as to correct the directions of gravity of images appearing on a monitor and thus enables correct stereoscopic-vision viewing. Compared with a right-and-left independent type endoscope in which right and left optical systems are installed independently, the pupil division type endoscope has a theoretical drawback in which parallax or a factor determining a sense of three-dimensionality of a view cannot be sufficiently provided. A magnitude of parallax depends on an angle of view whose value is defined in the specifications for a scope. Moreover, the magnitude of parallax is restrained directly by an image height and numerical aperture of a relay optical system which are determined by the thickness and length of an insertional part whose values are defined in the specifications for the scope. At present, a sense of three-dimensionality provided by the stereoscopic-vision endoscope is too weak. It seems to be impossible to provide a sense of three-dimensionality of a practically-acceptable level.

SUMMARY OF THE INVENTION

An object of the present invention is to provide a stereoscopic-vision endoscope capable of providing a magnitude of parallax permitting a sufficient sense of three-dimensionality that is unavailable in a pupil division type endoscope.

Another object of the present invention is to provide a stereoscopic-vision endoscope which can correct postures of images responsively to a change in direction of view resulting from the turn of an insertional part, and which enables reliable stereoscopic-vision viewing by correcting the directions of gravity of images appearing on a monitor and thus matching the directions of gravity with the direction of view irrespective of direct or skew viewing.

According to the present invention, the first structure includes an objective optical system composed of a front optical system including a field conversion optical system that has a single optical axis, and a rear optical system including an optical system that has a plurality of optical axes and receives a light beam from the front optical system so as to form a plurality of images on the optical axes.

According to the present invention, the second structure is such that the front optical system and the rear optical system can be turned relative to each other.

Other features and advantages of the present invention will be fully apparent from the description below.

BRIEF DESCRIPTION OF THE DRAWINGS

FIG. 6 is an explanatory diagram showing the overall configuration of a system including a stereoscopic-vision endoscope;

FIG. 7 is a longitudinal sectional view showing the structure of a major portion of the stereoscopic-vision endoscope;

FIGS. 8A to 8C and 9A to 9C are explanatory diagrams concerning the operation of the stereoscopic-vision endoscope and show the images used for stereoscopic-vision viewing;

FIGS. 20 to 22 relate to the second embodiment of the present invention;

FIG. 20 is a longitudinal sectional view showing the structure of a major portion of a stereoscopic-vision endoscope;

FIG. 22 is an explanatory diagram showing the layout of a back optical system, a stop means, and imaging devices;

FIGS. 23 and 24A to 24C relate to the third embodiment of the present invention;

FIG. 23 is a longitudinal sectional view showing the structure of a major portion of a stereoscopic-vision endoscope;

FIGS. 24A to 24C are explanatory diagrams concerning the operation of the stereoscopic-vision endoscope and show a procedure of forming right and left images;

FIG. 25 is a longitudinal sectional view showing the structure of a major portion of a stereoscopic-vision endoscope;

FIG. 26 is an explanatory diagram concerning the definitions of design data items concerning the optical system shown in FIG. 25;

FIG. 28 is a longitudinal sectional view showing the structure of a major portion of a stereoscopic-vision endoscope;

FIG. 29 is a sectional view showing the enlarged structure of an optical system located at the front end of the endoscope;

FIG. 30 is a sectional view along an optical axis showing the structure of a major portion of a stereoscopic-vision endoscope;

FIG. 31 is an explanatory diagram showing the definitions of design data items concerning the optical system shown in FIG. 30;

FIG. 32 is a longitudinal sectional view showing the structure of a major portion of a stereoscopic-vision endoscope;

FIG. 33 is an explanatory diagram concerning the operation of the stereoscopic-vision endoscope and shows image inversion resulting from the turn of an insertional part;

FIG. 34 is an explanatory diagram concerning the structure of a speed change gear mechanism for adjusting the quantities of rotation for an insertional part and imaging unit;

FIGS. 35A to 35C are explanatory diagrams concerning the operation of the stereoscopic-vision endoscope and show the quantity of rotation, by which the imaging unit is turned with the turn of the insertional part, and the positions of the imaging devices.

DETAILED DESCRIPTION OF THE PREFERRED EMBODIMENTS

FIGS. 6, 7, 8A to 8C, and 9A to 9C show the first embodiment of the present invention.

Figure 1:
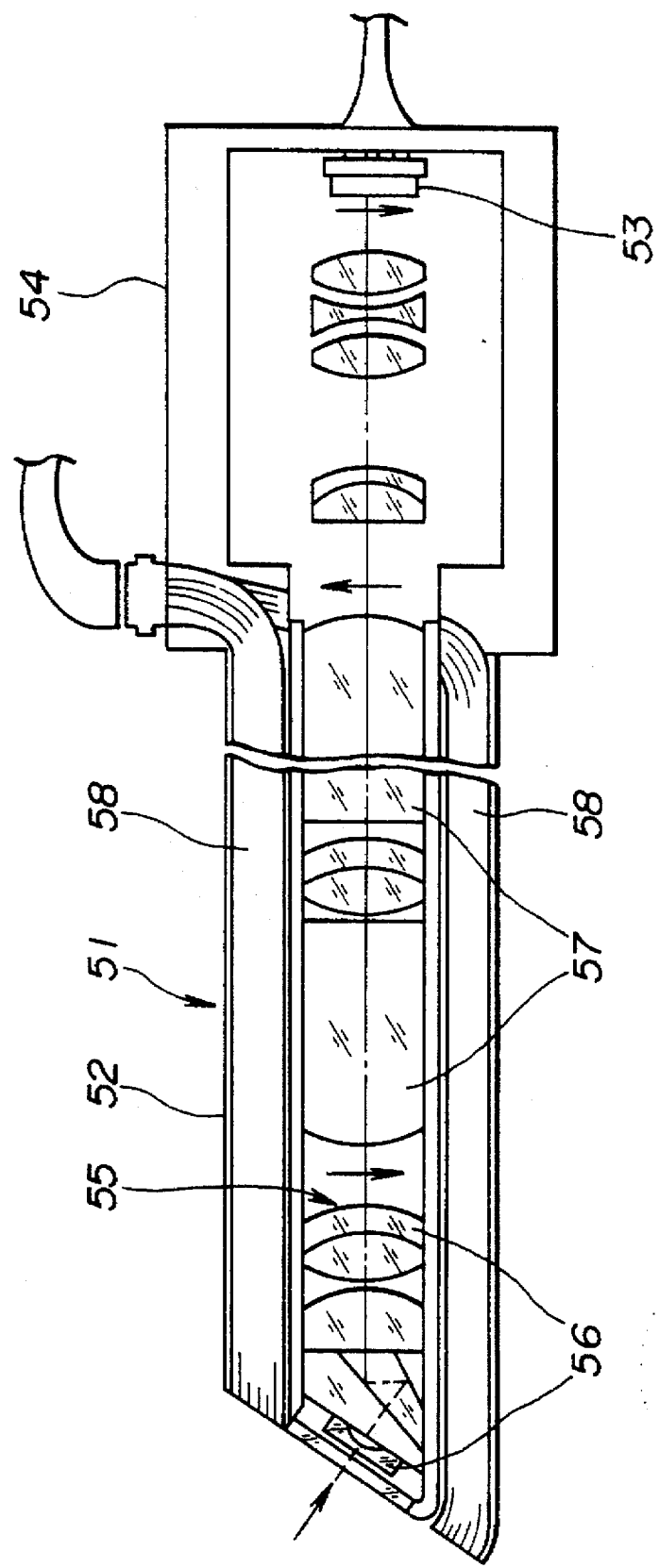
FIG. 1 is an explanatory diagram concerning the structure of an example of a conventional stereoscopic-vision endoscope.
Figure 2A:
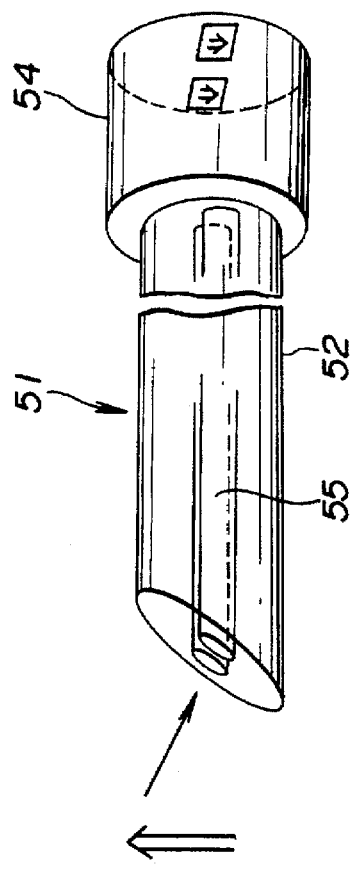
FIGS. 2A, 2B, 3A, and 3B are explanatory diagrams concerning the operation of the stereoscopic-vision endoscope shown in FIG. 1 and showing images produced for stereoscopic-vision viewing.
Figure 2B:
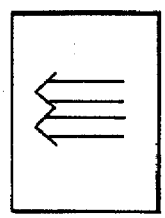
Figure 3A:
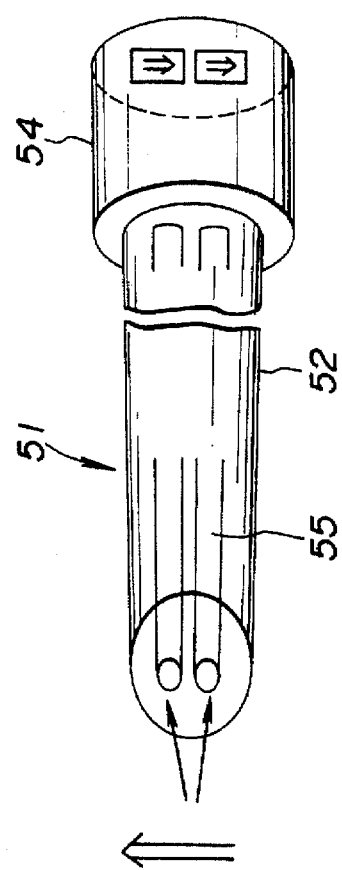
Figure 3B:
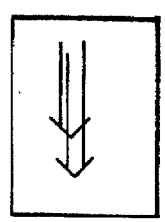
Figure 4:
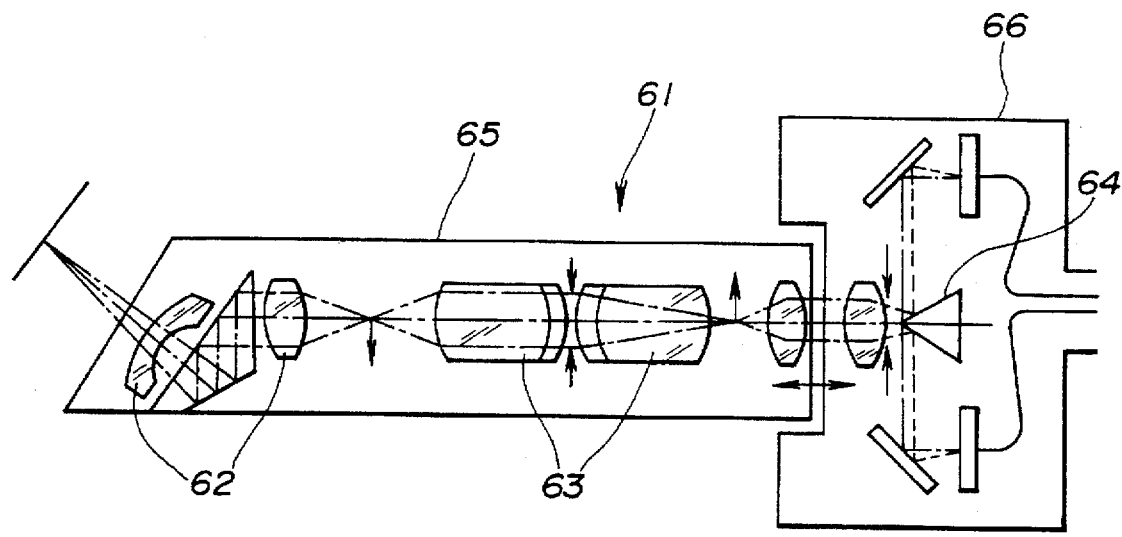
FIG. 4 is an explanatory diagram showing an example of the structure of a pupil division type stereoscopic-vision endoscope.
Figure 5:
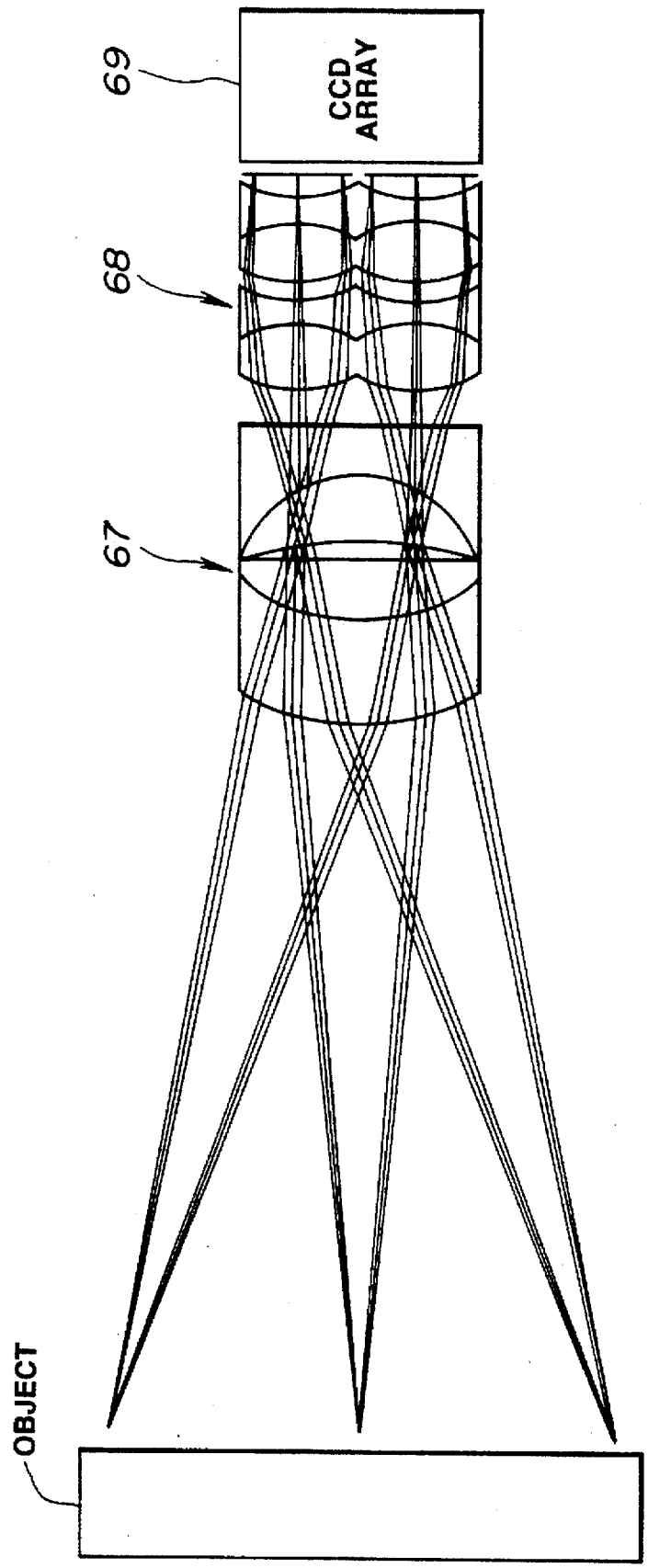
FIG. 5 is an explanatory diagram showing an example of the structure of a stereoscopic-vision endoscope having an optical system composed of two optical systems juxtaposed behind an optical system having a single optical axis.
Figure 6:
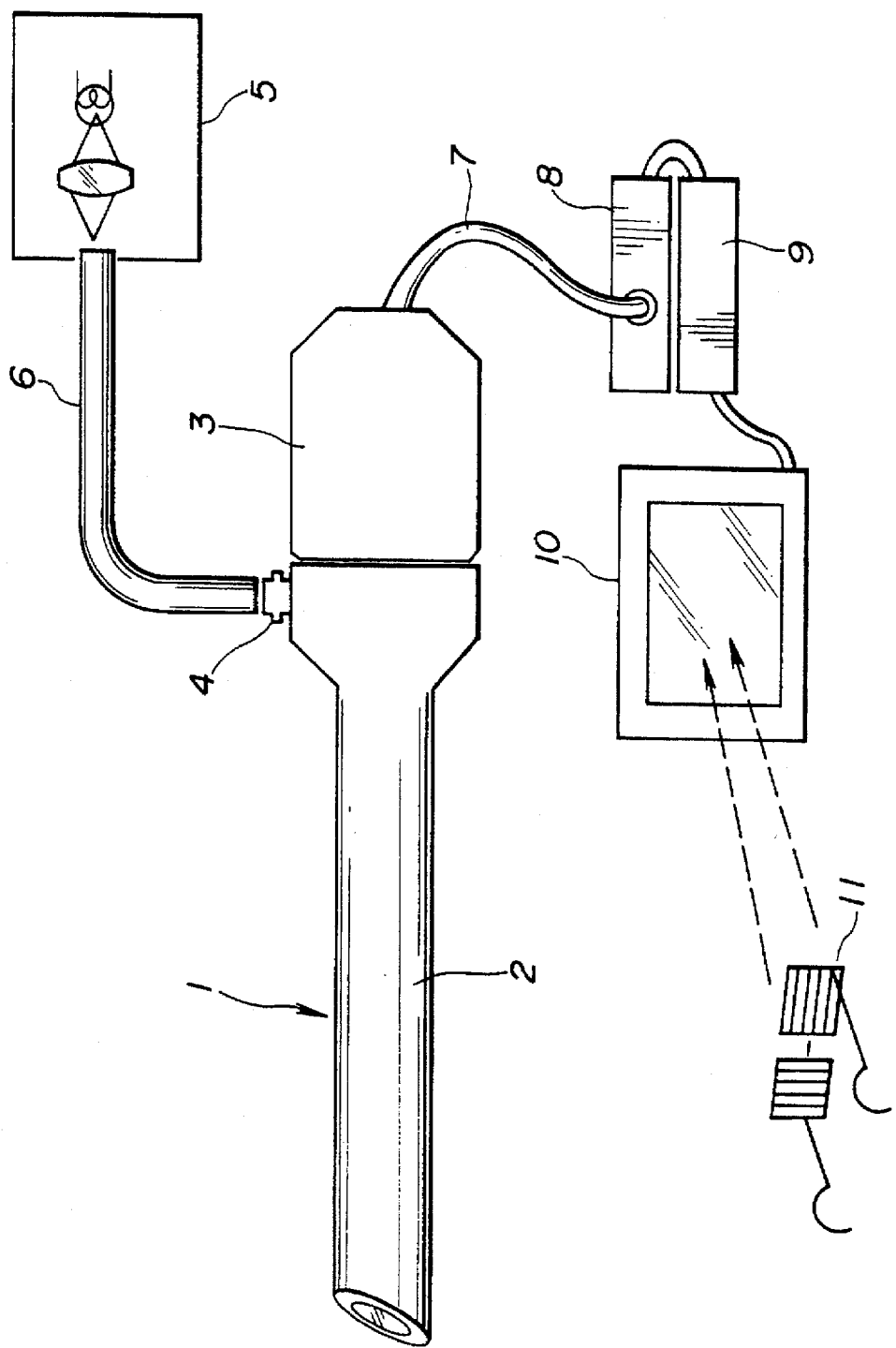
FIGS. 6, 7, 8A to 8C, and 9A to 9C relate to the first embodiment of the present invention.

As shown in FIG. 6, a stereoscopic-vision endoscope 1 of this embodiment has an elongated rigid insertional part 2. An operation unit 3 serving as a grip, which can be turned relative to the insertional part, is joined with to the proximal end of the insertional part 2. A light guide connector 4 is formed on the side of the proximal portion of the insertional part 2. A light guide cable 6 routed to a light source unit 5 is linked with the light guide connector 4, whereby illumination light emanating from the light source unit 5 is supplied.

A signal cable 7 is extending from the back end of the operation unit 3, and linked with a camera control unit 8. Right and left image signals resulting from photoelectric transform performed by imaging devices incorporated in the stereoscopic-vision endoscope 1 are fed to the camera control unit 8 and then subjected to various kinds of image signal processing. A speed-multiplication display monitor 10 is connected to the camera control unit 8 via a scan converter 9. Images corresponding to right and left eyes are alternately displayed on the monitor 10 at a multiplied speed. When the right and left images time-sequentially displayed on the monitor 10 are seen by a user when wearing glasses with shutters, which are opened and closed responsively to the right and left images on the monitor, so that only the images corresponding to the right and left eyes are visible to the right and left eyes, stereoscopic viewing is enabled.

A three-dimensional image display system is not limited to the configuration made up of the scan converter 9, monitor 10, and glasses with shutters 11. Alternatively, a polarization unit such as a polarization filter may be attached to a monitor and used to modulate right and left images to be displayed on the monitor. This results in polarized light components that are mutually orthogonal. In this case, a viewer wears polarization glasses for transmitting the polarized light components corresponding to his/her right and left eyes, whereby stereoscopic viewing is enabled. Otherwise, a compact monitor may be attached to each of the right and left sides of glasses or the like to be mounted on a viewer's head. Right and left images are displayed on the monitors, whereby stereoscopic viewing is enabled.

Figure 7:
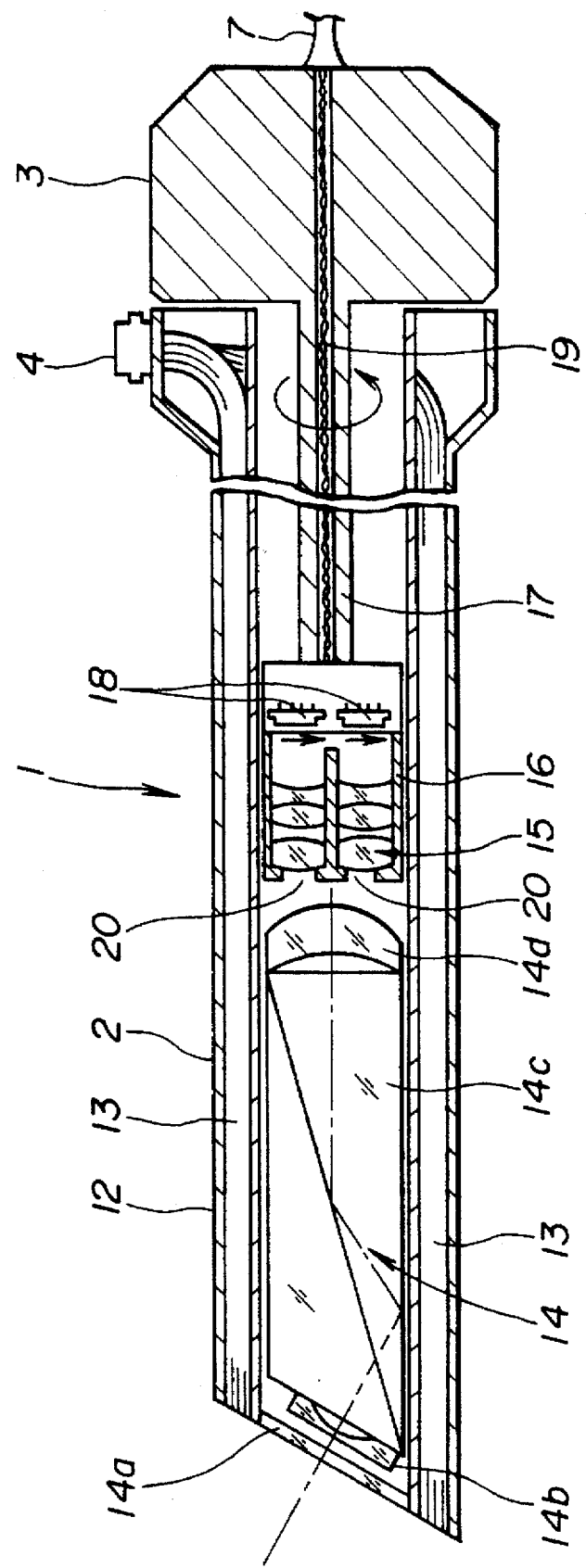

FIG. 7 shows the structure of a major portion of the stereoscopic-vision endoscope 1. In the insertional part 2 that is a main unit of the stereoscopic-vision endoscope 1, the light guide 13 is extending from the light guide connector 4 to the distal end of the insertional part 2 within an armor tube 12. A main optical system 14 having a single optical axis is placed within the inner circumference of the light guide 13. A rotary unit 16 serving as an optical system assembly, which includes a rotary optical system 15 that has right and left optical axes and can be turned relative to the main unit of the endoscope, is placed in the space behind the main optical system 14 in the insertional part 2. The rotary unit 16 is united with the operation unit 3 via a bar-like coupler 17. Imaging devices 18 for photoelectrically transforming right and left images formed by the optical systems are incorporated in the rotary unit 16. A signal line 19 running through the signal cable 7 is linked to the imaging devices 18, whereby the imaging devices 18 are electrically connected to the camera control unit 8.

Illumination light emanating from the light source unit 5 is transmitted to the distal end of the endoscope over the light guide cable 6 and the light guide 13 in the endoscope. The light is then irradiated to an object of viewing. The object is clearly illuminated. An image of the object illuminated is formed as right and left images causing parallax by means of the main optical system 14 and rotary optical system 15, and then transformed into electrical signals by the imaging devices 18. The signals are then sent to the camera control unit 8 and subjected to various kinds of signal processing. This results in right and left image signals. The right and left image signals are displayed by the three-dimensional image display system composed of the scan converter 9, monitor 10, and Glasses with shutters 11. The object of viewing can be discerned as a three-dimensional image.

During viewing, when the operation unit 3 of the stereoscopic-vision endoscope 1 is rotated relative to the insertional part 2, the rotary unit 16 situated behind the main optical system 14 locked in the insertional part 2 can be rotated relative to the main optical system 14.

For enabling correction of postures of images while ensuring a sufficient sense of three-dimensionality, the arrangement of the optical systems for the stereoscopic-vision endoscope of this embodiment has the features described below. The main optical system 14 locked in the main unit of the endoscope is an optical system having a single optical axis. The rotary optical system 15 that can be rotated relative to the optical system 14 is composed of right and left optical systems having different optical axes which are juxtaposed. The optical systems extract rays causing parallax from a light beam transmitted by the main optical system 14 located in front of the optical systems, and form right and left independent images. The imaging devices 18 for receiving the right and left images formed by the rotary optical systems having right and left optical axes and photoelectrically transforming the images are placed behind the rotary optical system 15. Alternatively, the right and left images formed may be received directly by the imaging devices, or a relay optical system may be placed in front of the imaging devices so that the imaging devices can received images relayed by the relay optical system.

The rotary unit 16 has apertures 20, which define right and left light beams that cause parallax and travel in the rotary optical system 15, at positions from which the right and left axes of the rotary optical system 15 extend. The apertures 20 are rotated responsively to the rotation of the rotary unit 16. A light beam emanating from the main optical system 14 is divided into two light beams causing parallax because of the apertures 20.

Since the optical systems are arranged as mentioned above, when the rotary unit 16 is rotated relative to the main optical system 14, the apertures 20 serving as light intake ports and forming right and left images are turned accordingly. This enables correction of postures of images. The correction of the postures of images are illustrated in FIGS. 8A to 8C and 9A to 9C.

Figure 8C:
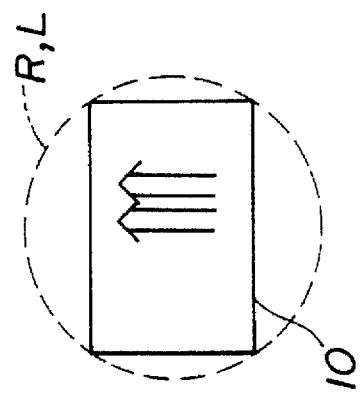
Figure 8B:
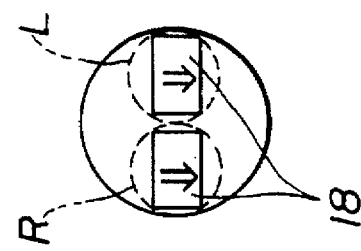
Figure 8A:
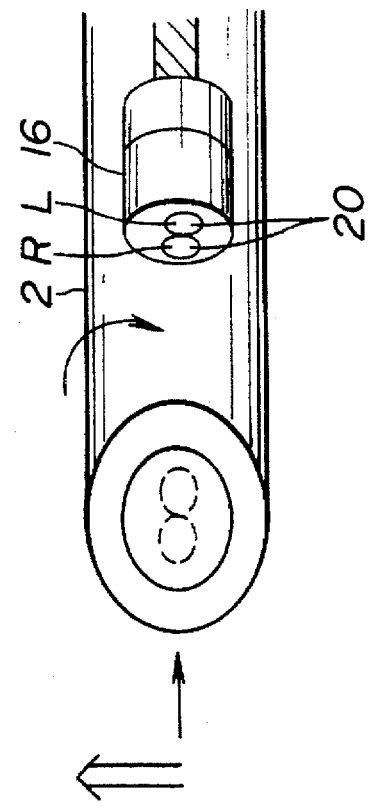

As shown in FIG. 8A, when the distal end of the insertional part is oriented upward (vertically), the direction of gravity of a region to be viewed (an object is indicated with an arrow) is consistent with the orientation of the distal end of the insertional part. The right and left (R and L) apertures 20 of the rotary unit 16 are horizontally juxtaposed horizontally. As shown in FIG. 8B, images whose directions of gravity are consistent with the direction of gravity of the object (images in FIG. 8B are inverted) are projected on the right and left (R and L) imaging devices 18. As shown in FIG. 8C, the right and left images whose directions of gravity are consistent with the direction of gravity of the object are displayed on the monitor 10. Consequently, stereoscopic-vision viewing can be achieved with the directions of gravity of images on the monitor consistent with the direction of gravity of the object.

Figure 9C:
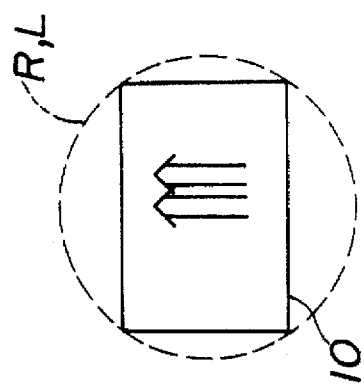
Figure 9B:
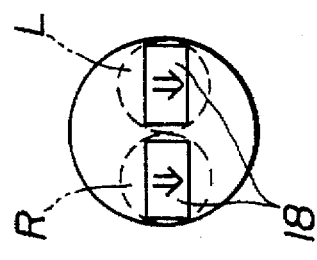
Figure 9A:
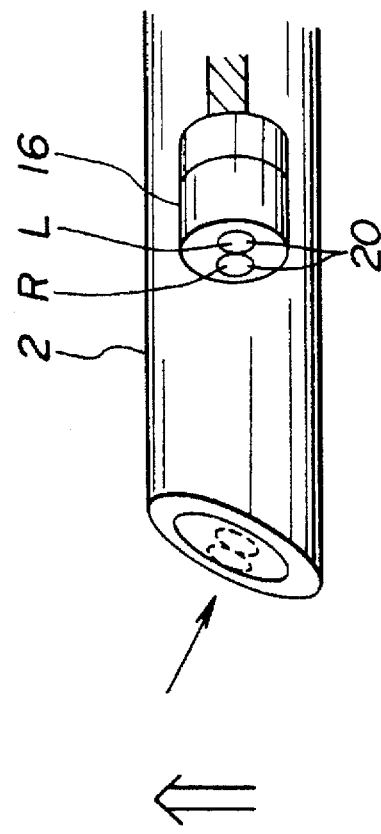

When the insertional part 2 in the state of FIG. 8A is rotated as a whole in order to orient the distal end of the insertional part sideways (laterally), the formed images of the object are rotated 90°. Consequently, the directions of images on the monitor become inconsistent with that of the object. In this embodiment, as shown in FIG. 9A, the rotary unit 16 is turned relative to the main optical system 14 in the insertional part 2 so that the apertures 20 will be horizontally juxtaposed in the same manner as those shown in FIG. 8A. Consequently, as shown in FIGS. 9B and 9C, the directions of gravity of images on the monitor become consistent with the direction of gravity of the region to be viewed.

At this time, the direction in which the right and left apertures are juxtaposed must be orthogonal to the direction of gravity of the region to be viewed, and the vertical directions of the imaging surfaces of the imaging devices must be consistent with the direction of gravity of the region to be viewed. Under these important conditions, the directions of gravity of images on the monitor become consistent with that of the region to be viewed.

When the diameter of a light beam traveling in the main optical system 14 is determined to such an extent that the diameter will cover the diameters of light beams passing through the two apertures 20 of the rotary unit 16, even if the rotary unit 16 is rotated to any position, it will not occur that rays are obstructed to cause vignetting and make parts of images invisible.

When a field conversion optical system including a skew-view prism is placed in the main optical system, the postures of images can be corrected during skew viewing. As for a structure in which right and left independent optical systems are included and an optical system designed for skew viewing is included in each of the optical systems, when an insertional part is rotated in order to change the direction of view for the purpose of skew viewing, the optical systems are rotated about the axis of an insertional part. In this case, parallax resulting from right and left images occurs in a vertical direction due to images on a monitor. This disables stereoscopic viewing. According to the structure of this embodiment, the postures of images can be corrected properly irrespective to the direction of skew viewing. Reliable stereoscopic viewing can be achieved.

Now, the basic arrangement of optical systems responsible for image posture correction will be described.

Figure 10:
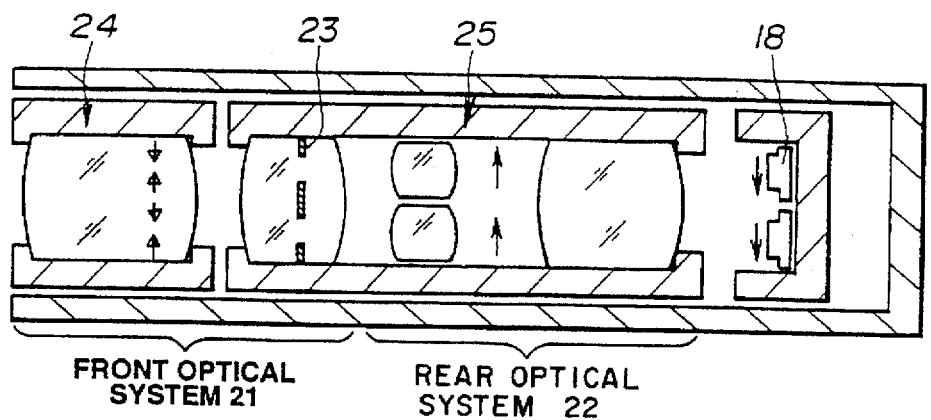
FIG. 10 is an explanatory diagram showing the basic structure of an optical system enabling correction of postures of images.

FIG. 10 shows a basic structure serving as an optical system for enabling correction of postures of images. The optical system comprises a front optical system 21 which is an optical system which lies on the front side and whose elements share the same light path or the same optical axis, and a rear optical system 22 juxtaposed behind the front optical system 21 and composed of right and left optical systems having different optical axes. The optical system whose elements share the same optical axis is an angle-of-view conversion optical system composed of afocal lenses or the like.

The right and left optical systems being juxtaposed and having different optical axes receive a light beam from the optical system which lies ahead of the right and left optical systems and whose elements share the same optical axis, and form right and left independent images of an object causing parallax. The back rear optical system 22 may include a relay means for transmitting the right and left images further backward. The right and left images formed by the back optical system 22 are picked up by the imaging devices 18 lying behind the back optical system 22 and converted into electrical signals.

A stop means 23 having a plurality of apertures for defining right and left light paths is situated within the front optical system 21 or ahead of the optical systems of the back optical system 22 which are juxtaposed and have different optical axes. In an alternative structure, entrance pupils of the stop means located in the back optical system 22 may be projected on the front optical system 21.

For efficiently correcting positions of images by compensating for the turn of the images, the front optical system 21 is mounted in a front assembly 24 (equivalent to the main optical system 14) locked in the main unit or the insertional part, while the back optical system 22 is mounted in a back assembly 25 (equivalent to the rotary optical system 15) that can be rotated relative to the main unit or the insertional unit. As shown in FIG. 10, a portion of the front optical system 21 may be mounted in the back assembly 25.

The front assembly 24 accommodates only the optical system whose elements share the same optical axis. Even when a light path is moved with the rotation of the insertional part, the light path is wide enough to pass rays traveling within a given range without obstructing the rays. The stop means 23 for substantially defining the right and left light paths is placed in the back assembly 25. The right and left optical systems having different optical axes are located behind the stop means 23. The right and left optical systems form right and left independent images causing parallax. The imaging devices 18 need not always be rotated together with the back assembly 25. In this embodiment, the imaging devices 18 are rotated together with the back assembly 25. When the imaging devices 18 are not rotated together with the back assembly 25, the turn of the insertional part may lead to vignetting or rotated images. Some measures must therefore be taken.

Next, senses of three-dimensionality permitted by the basic arrangements of optical systems in this embodiment and of pupil division type optical systems will be described.

According to the arrangement of optical systems in this embodiment, an angle-of-view conversion optical system such as an afocal optical system is used as the front optical system. Even if the values of the angle-of-view and diameter of a rigid endoscope are defined in the specifications for the rigid endoscope, the angles-of-view permitted by the angle-of-view conversion optical system and rear optical system determine the angle of view permitted by the rigid endoscope. The distance between the right and left optical axes can therefore be retained independently of the angle-of-view, which will be described in detail later. The magnitude of parallax can therefore be modified or set to an optimal value irrespective of the angle of view of the whole of the optical systems. Compared with the pupil-division type optical systems, the optical systems in this embodiment can provide a large magnitude of parallax with an angle-of-view whose value is defined in the specifications for the rigid endoscope.

Figure 11:
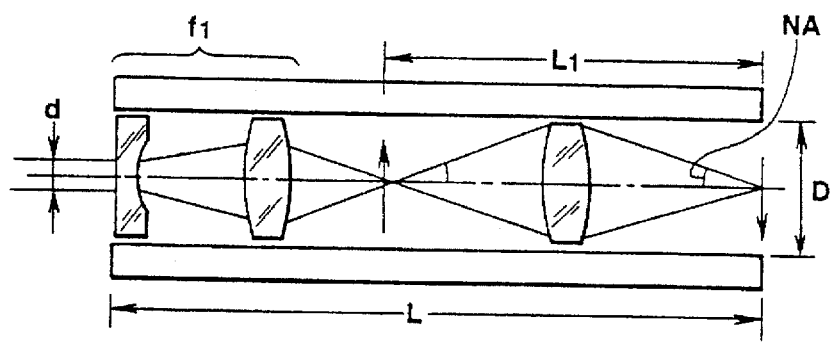
FIG. 11 is an explanatory diagram showing the basic structure of a pupil division type optical system.

In comparison with this embodiment, a sense of three-dimensionality permitted by the pupil division type optical systems will be described. FIG. 11 shows the basic arrangement of pupil division type optical systems.

Assume that the effective length of a stereoscopic-vision endoscope is L, the diameters of lenses are D, the focal length of an objective optical system is f1, and the angle-of-view is $2\omega$. Taking an ordinary laparoscope for instance, L equals to 300 mm, D ranges from 6 to 7 mm, and $2\omega$ ranges from 60° to 70°. Herein, D shall equal to 7 mm and $2\omega$ shall equal to 60°.

The focal length f1 of an objective optical system, angle of view $2\omega$, and image height h have the following relationship:

$$h = f1 \cdot \tan\omega$$

The image height h does not exceed a value of D/2 and is usually set to the range of values expressed as $D/2 > h > D/4$. The larger the value h, the more intense the sense of three-dimensionality becomes. Herein, the image height h shall be equal to the value of D/2.

Supposing that the number of relays is one, the relay length L1 of a relay optical system is about half of the effective length L of a stereoscopic-vision endoscope, and ranges from 150 to 200 mm. The larger the numerical aperture NA of the relay optical system is, the more intense the sense of three-dimensionality becomes. Herein, the relay length L1 shall equal to 150 mm.

Using the above parameters, the diameter d of an entrance pupil can be expressed as follows:

$$d = f1 \cdot NA \cdot 2 = h/\tan\omega \cdot NA \cdot 2 = D/2/\tan\omega \cdot D/L1 \cdot 2$$
$$= D^2/\tan\omega \cdot 1/L1$$

When the above values of the parameters are assigned to the above expression, $$d = (3.5)^2/\tan 30° \cdot 1/150 \approx 0.14 \text{ mm}$$

Figure 12:
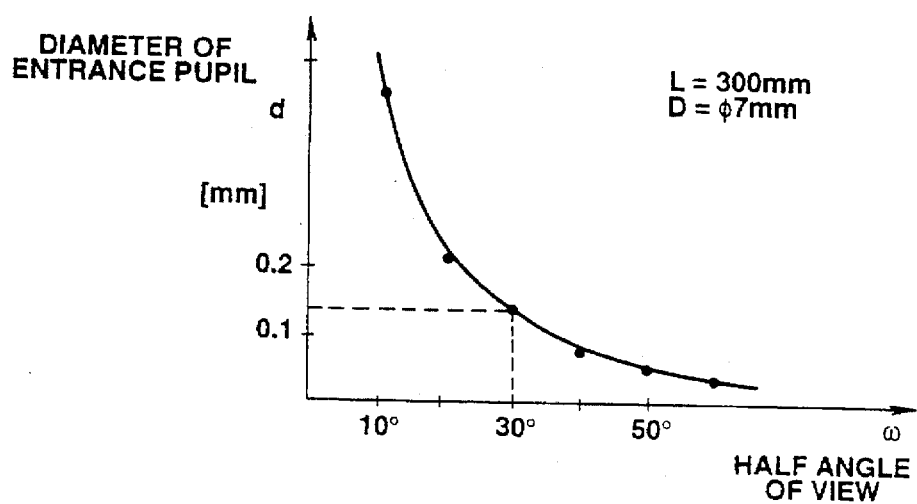
FIG. 12 shows a characteristic curve expressing the relationship between the diameter of an entrance pupil and the half-angle of-view for the pupil division type optical system.

FIG. 12 shows the relationship between the diameter d of an entrance pupil and the half-angle of view $\omega$ which are calculated according to the above expression. As seen from the characteristic graph of FIG. 12, the diameter d of an entrance pupil is substantially inversely proportional to the half-angle of view $\omega$. The diameter d of an entrance pupil therefore varies depending on the angle-of-view $2\omega$. In the pupil division type, right and left light paths are defined within the diameter d of an entrance pupil. The distance between the right and left optical axes will therefore not exceed the d value and is slightly lower than the d value in practice. As far as the pupil division type is concerned, the distance between optical axes determining the magnitude of parallax providing a sense of three-dimensionality varies directly depending on the angle-of-view.

Supposing that the number of relays is increased from one to three, the distance between the right and left optical axes becomes three times larger. The number of relays may be 1, 3, 5, etc. or an odd value. However, because the effective length L of a stereoscopic-vision endoscope is fixed and influence of aberration must be taken into consideration, the upper limit of the number of relays is determined. Normally, the upper limit is three.

Figure 13:
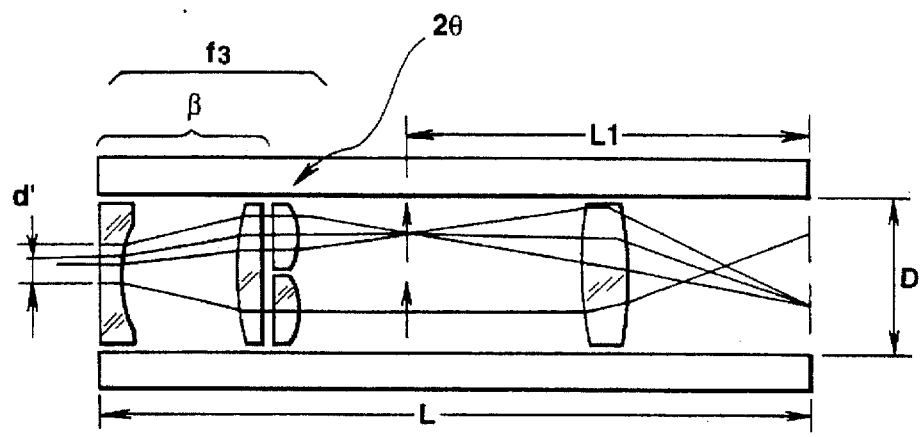
FIG. 13 is an explanatory diagram showing the basic structure of an optical system for the stereoscopic-vision endoscope of this embodiment.

Next, the sense of three-dimensionality permitted by the optical systems of this embodiment will be described. FIG. 13 shows the basic arrangement of the optical systems of this embodiment.

Assume that the effective length of a stereoscopic-vision endoscope is L, the diameters of lenses are D, the focal length of an objective optical system (a composite focal length of focal lengths of the front optical system and back optical system) is f3, and the angle-of-view is $2\omega$. Similarly to the above description of the pupil division type optical systems, a laparoscope is taken for instance. L shall equal to 300 mm, D shall range from 6 to 7 mm, and $2\omega$ shall range from 60° to 70°.

The composite focal length f3, angle of view $2\omega$, and image height h have the relationships below.

$$h = f3 \cdot \tan\omega$$

Figure 14:
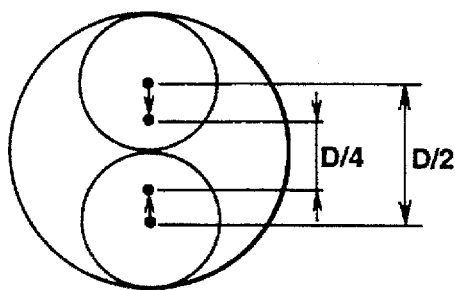
FIGS. 14 and 15 are explanatory diagrams concerning the relationships between the image height and the diameters of entrance pupils formed on right and left light paths.
Figure 15:
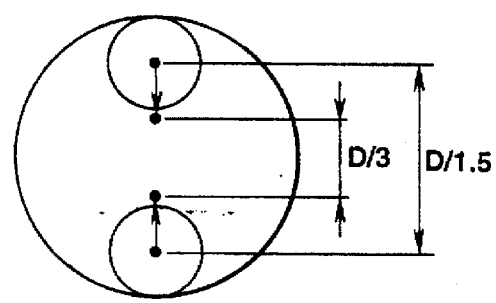

Even when the diameter of each of entrance pupils on the right and left light paths is, as shown in FIG. 14, maximized in order to obtain a maximum image height, the image height h cannot exceed a value D/4. When the diameter of each of entrance pupils on the right and left paths is, as shown in FIG. 15, minimized in order to obtain a minimum image height, the distance between the right and left optical axes in the back optical system can be widened. This leads to a more intense sense of three-dimensionality. However, images become smaller, image quality deteriorates.

Assuming that the front optical system is substantially an afocal optical system, the angular magnification is $\beta$, and the angle-of-view permitted by the rear optical system is $2\theta$, the angle-of-view $2\omega$ permitted by the front optical system and back optical system is provided by the relational expression below.

$$\tan\omega = \tan\theta / \beta$$

Even when the angle-of-view $2\omega$ is defined in the specifications for a rigid endoscope, the angular magnification $\beta$ and the angle of view $2\theta$ permitted by the back optical system can be modified freely. By modifying the $\beta$ and $2\theta$ values, the distance between the right and left optical axes can be varied. Unlike the pupil division type optical systems, a maximum magnitude of parallax is not determined directly with the angle-of-view. The distance between the right and left optical axes can be set to an optimal value.

Assume that the image height h equals to D/4, the distance between the right and left optical axes in the back optical system is D/2, the angular magnification $\beta$ equals to ½, and the angle of view $2\theta$ is 60°. In this case, the half angle of view $\theta$ permitted by the back optical system is 15°. Under these conditions, the distance d' between the right and left optical axes in the object space is expressed as follows:

$$d' = \beta \cdot D/2 = \tfrac{1}{2} \cdot D/2 = D/4$$

If D equals to 7 mm, the distance d' is calculated as follows:

$$d' = \tfrac{7}{4} = 1.8 \text{ mm}$$

Figure 16:
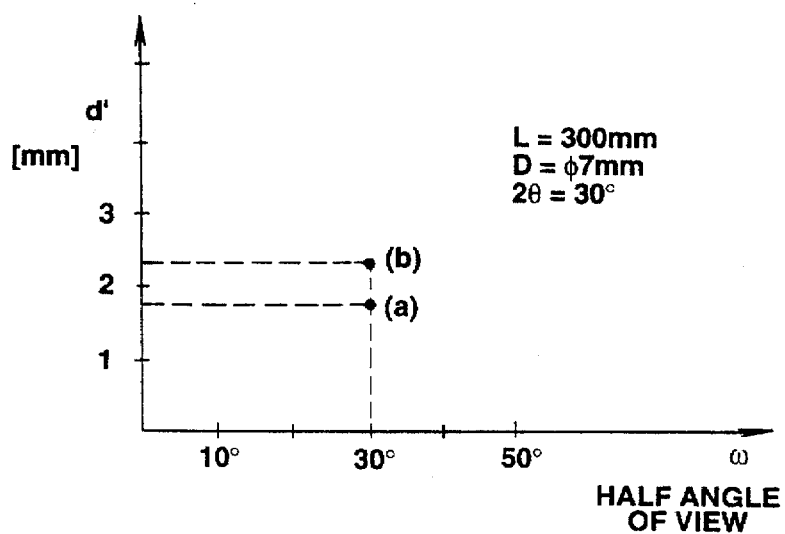
FIG. 16 is a characteristic graph showing the relationships between the distance between right and left optical axes in the object space of an optical system of this embodiment and the half-angle of-view.

FIG. 16 shows the relationship between the distance d' between the right and left optical axes in the object space and the half-angle of view $\omega$ which are calculated according to the above expression. As apparent from the characteristic graph of FIG. 16, the distance d' between the right and left optical axes does not depend on the angle-of-view permitted by an objective optical system, but can be varied by modifying the angular magnification $\beta$ permitted by the front optical system and the angle-of-view $2\theta$ permitted by the back optical system.

Compared with the pupil division type optical systems, the optical systems in this embodiment make it possible to set a distance between right and left optical axes, which determines the magnitude of parallax providing a sense of three-dimensionality, to about several to several tens times a larger value in practice. According to the arrangement of optical systems in this embodiment, not only the aforesaid correction of postures of images is enabled but also a sufficiently large distance between right and left optical axes can be ensured. A sufficient sense of three-dimensionality can therefore be provided, thus enabling appropriate stereoscopic visioning. A smaller image height leads to slightly deteriorated image quality. However, when the distance between optical axes in the back optical system is widened, the magnitude of parallax increases.

Next, the basic arrangement of optical systems for enabling skew viewing will be described.

For skew viewing, in this embodiment, a field conversion optical system such as a skew-view prism is included in a front optical system. As mentioned above, for the optical systems in this embodiment, a stop means for defining right and left light paths and separating the light paths so that rays will not be mixed up is rotatably united with optical systems constituting a rear optical system, being juxtaposed, and having right and left independent optical axes. It is normally impossible to place the stop means within a skew-view prism. The stop means is therefore positioned behind the skew-view prism.

The front optical system is required to transmit a large-diameter light beam, so that right and left light paths can be created in the succeeding stage. The skew-view prism is therefore constructed so that it can pass a large-diameter light beam. For preventing the light beam traveling through the skew-view prism from being obstructed, optical systems must be arranged by taking account of two points: that a stop be placed in front of a rear optical system, and that a convex lens be placed in front of right and left optical systems having independent optical axes in order to shrink the distance between the optical axes. Specifically, the angle-of-view $2\theta$ permitted by the back optical system is set to a smaller value than the angle of view $2\omega$. In addition, the angular magnification $\beta$ permitted by the front optical system is set to a smaller value.

When an attempt is made to reserve light paths, the position of a stop may be thought to be inside the skew-view prism. In this case, because it is impossible to place a stop member inside the prism, a stop member having one aperture is placed at a position in a relay optical system conjugate to the position at which the stop must be placed. In this structure, when the light paths are traced back, entrance pupils of the stop member placed in the relay optical system are projected on the prism by two optical systems constituting the back optical system. Thus, the same situation as the one in which entrance pupils of two apertures are formed is set up. The same effect as that exerted when a stop member having two apertures is placed inside the prism is exerted.

In other words, a relay optical system relays images transmitted by right and left juxtapositional optical systems as well as entrance pupils formed thereby. The right and left entrance pupils are projected on a skew-view prism. Herein, a stop is placed in a relay optical system so that it will share the same optical axis with the relay optical system.

The adoption of the aforesaid basic arrangement of optical systems enables the correction of postures of images, which is an object of this embodiment, permits a sufficient sense of three-dimensionality, and realizes skew viewing. Eventually, a stereoscopic-vision endoscope that will not pose any problem for practical application is made available.

Returning to FIG. 7, the practical arrangement of optical systems for a stereoscopic-vision endoscope of this embodiment will be described.

A main optical system 14 serving as a front optical system is an optical system composed of a cover glass 14a, a plano-concave lens 14b, a 30° skew-view prism 14c, and a meniscus convex lens 14d, which are arranged in that order from the distal end of the endoscope and share one optical axis. The front optical system is locked in and united with the insertional part 2 of the stereoscopic-vision endoscope, thus constituting a front assembly.

Because to the front optical system includes the 30° skew-view prism 14c, the direction of skew viewing permitted by the optical systems of the stereoscopic-vision endoscope 1 of this embodiment is set to 30°. The 30° skew-view prism 14c is made by joining two prisms using an adhesive. Light entering through the plano-concave lens 14b is transmitted by the composition plane of the prism 14c, reflected from the bottom thereof, totally reflected by the composition plane thereof, and thus angled toward the meniscus convex lens 14d.

A rotary optical system 15 serving as a rear optical system is composed of a pair of optical systems juxtaposed in order to form right and left images causing parallax. The elements of each of the right and left optical systems share the same optical axis. Each of the right and left optical systems is an image formation optical system consisting of a convex lens and a meniscus lens having a composition plane. The back optical system receives a light beam from a front optical system and forms right and left images.

A stop means having two apertures 20 for separating a right light beam from a left light beam is interposed between the front and rear optical systems.

Right and left images formed by the rear optical system are picked up by a pair of right and left imaging devices 18 situated in a rotary unit 16. The right and left images transformed into electrical signals by the right and left imaging devices 18 are displayed on a monitor 10.

The rotary unit 16 that can be rotated accommodates the rotary optical system 15, stop means having the apertures 20, and imaging devices 18, and communicates with an operation unit 3 via a coupler 17. With the turn of the operation unit 3, all the components in the rotary unit 16 are turned as a united body relative to the main optical system 14 in the insertional part 2.

With the turn of the rotary unit 16, a light path in the front optical system leading to right and left light paths in the back optical system moves circumferentially. A light path that is wide enough to pass a large-diameter light beam should be prepared for fear that the light paths be obstructed.

A signal line 19 over which output signals provided by the imaging devices 18 are transmitted is routed to an external camera control unit 8 through the operation unit 3.

The signal line 19 is incorporated in a tubular torque transmission member constituting the coupler 17 for use in turning the rotary unit 16, whereby a simple structure is realized.

According to the structure of this embodiment, the rotary unit 16 including the rear optical system and the operation unit 3 are united with each other. The front optical system is locked in and united with the insertional part 2. These two assemblies are independent of each other. An operating assembly including the operation unit 3 may be detached from a main assembly including the insertional part 2. The operating assembly may be detached from the main assembly, and then be attached to another main assembly including an optical system having a prism that permits a different direction of a field. Thus, a detachable structure can be realized. The rotary unit 16 and operation unit 3 can be used in common to a plurality of insertional parts of stereoscopic-vision endoscopes offering different directions of skew viewing.

Figure 17:
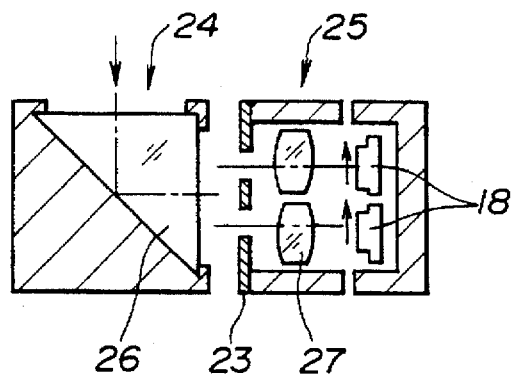
FIG. 17 is an explanatory diagram showing the structure of the first variant of the optical system of this embodiment.
Figure 18:
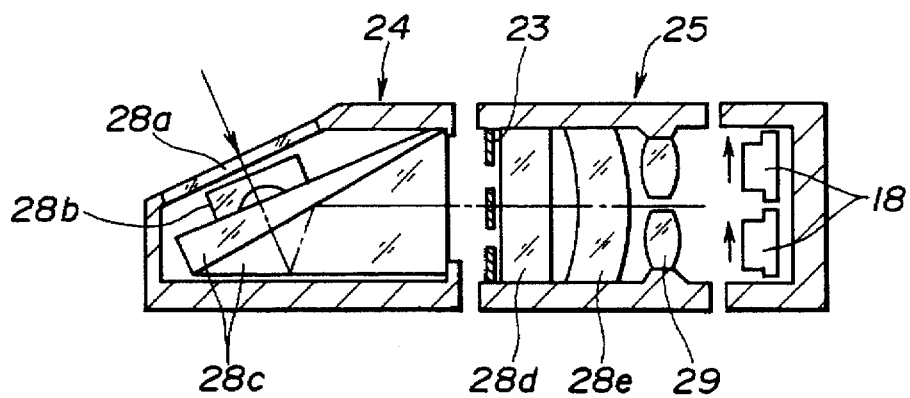
FIG. 18 is an explanatory diagram showing the structure of the second variant of the optical system of this embodiment.
Figure 19:
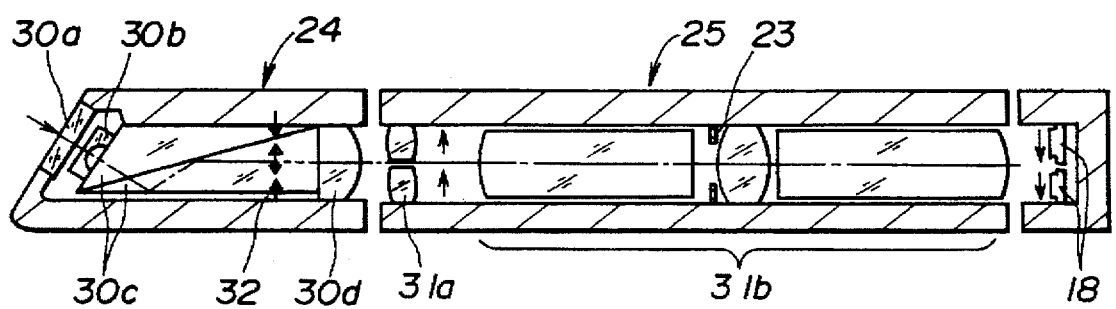
FIG. 19 is an explanatory diagram showing the structure of the third variant of the optical system of this embodiment.

FIGS. 17 to 19 show variants of the arrangement of optical systems. In the first variant of FIG. 17, a rectangular prism 26 is used as a front optical system, and juxtapositional convex lenses 27 are used as a back optical system. Included in a front assembly 24 is an optical system whole elements provide a common light path; that is, the rectangular prism 26. The convex lenses 27 juxtaposed in order to form right and left images, and a stop means 23 having two apertures for defining right and left light paths are included in a back assembly 25. Imaging devices 18 are placed on the right and left paths behind the back assembly 25.

In the second variant of FIG. 18, a parallel cover glass 28a, a plano-concave lens 28b, a 70° prism 28c, a parallel prism 28d, and a meniscus convex lens 28e are installed as an optical system which serves as a front optical system and of which elements provide a common light path and share the same optical axis. Convex lenses 29 are juxtaposed to constitute a rear optical system. A front assembly 24 includes the cover glass 28a, concave lens 28b, and 70° prism 28c which constitute the front optical system. A back assembly 25 includes the parallel prism 28d and meniscus convex lens 28e which constitute the front optical system, and the convex lenses 27 juxtaposed in order to constitute the rear optical system. In the rear assembly 25, a stop means 23 having two apertures for defining right and left light paths is placed in front of the parallel prism 28d. Imaging devices 18 are situated behind the rear assembly 25 in the same manner as those in the variant of FIG. 17.

In the third variant of FIG. 19, a parallel cover glass 30a, a plano-concave lens 30b, a 30° skew-view prism 30c, and a plano-convex lens 30d constitute an optical system which serves as a front optical system and of which elements provide a common light path and share the same optical axis. Juxtapositional convex lenses 31a, and a system of relay lenses 31a composed of a plano-convex rod lens, convex lens, and plano-convex lens constitute a rear optical system. A front assembly 24 includes the parallel cover glass 30a, plano-concave lens 30b, 30° skew-view prism 30c, and plano-convex lens 30d which constitute the front optical system. A back assembly 25 includes the juxtapositional convex lenses 31a and system of relay lenses 31b which constitute the rear optical system.

The rear assembly 25 has a stop means 23 situated in the system of relay lenses 31b. The stop means 23 projects right and left entrance pupils, which are formed by the right and left juxtapositional optical systems, on the 30° skew-view prism 30c. A stop providing right and left entrance pupils is situated within the rear assembly. Imaging devices 18 are placed behind the rear assembly 25 in the same manner as those in the variant of FIG. 17.

Thus, various variants are conceivable as the arrangement of optical systems enabling correction of postures of images and including a field conversion optical system.

As mentioned above, according to the arrangement of optical systems in this embodiment, a magnitude of parallax permitting a sufficient sense of three-dimensionality, which is unavailable in a pupil division technique, can be provided for a stereoscopic-vision endoscope using another technique. A rear optical system having two optical axes and forming right and left images can be rotated relative to a front optical system having a single optical axis. The postures of images in the direction of rotation of the images can therefore be corrected responsively to a change in direction of view resulting from the turn of an insertional part. Consequently, as far as direct viewing is concerned, the directions of gravity in images can be corrected merely by turning a proximal operation unit with a main unit of a stereoscopic-vision endoscope held at a desired angular position. Not only for direct viewing but also for skew viewing, when the main unit of a stereoscopic-vision endoscope is turned and angled in a desired direction of viewing, the directions of gravity in images appearing on a monitor can be corrected without vignetting or the loss of a sense of three-dimensionality.

Figure 20:
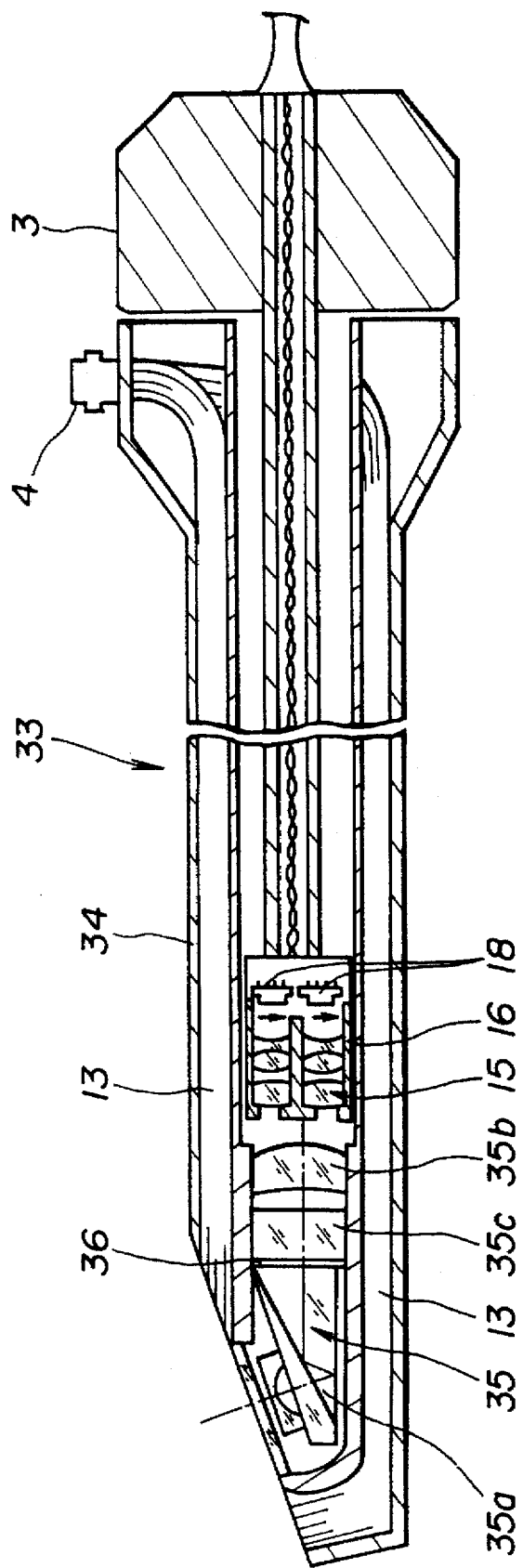
Figures 21A, 21B:
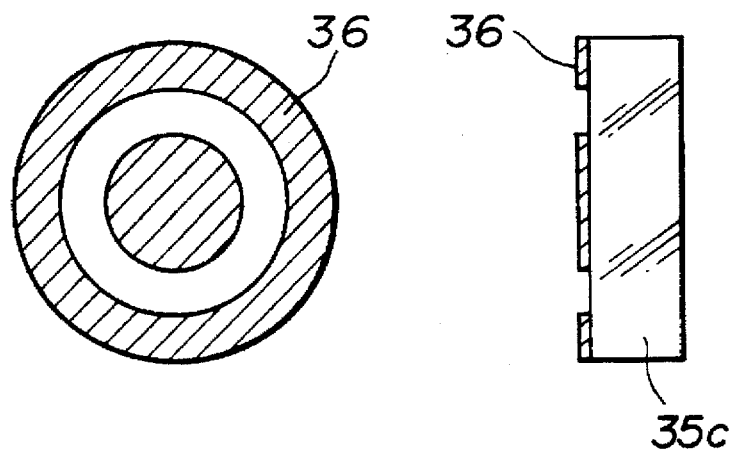
FIGS. 21A and 21B are explanatory diagrams showing the structures of a flare stop serving as a stop means.
Figure 22:
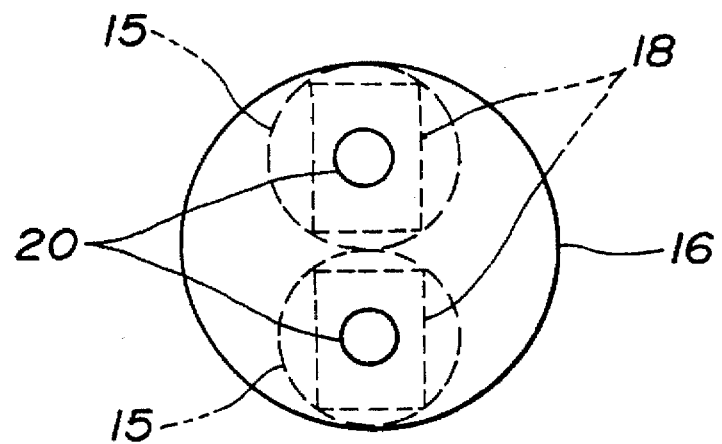

FIGS. 20 to 22 show the second embodiment of the present invention.

In the second embodiment, the structure of the front optical system of optical systems in the first embodiment is modified.

A stereoscopic-vision endoscope 33 of this embodiment is structured so that an operation unit 3 coupled to a rotary unit 16 having the same structure as that in the first embodiment can be rotated relative to an insertional part 34 in which a front optical system is locked.

A main optical system 35 serving as a front optical system and having a single optical axis is incorporated in the insertional part 34. The main optical system 35 has, unlike the one in the first embodiment, a 70° prism 35a used for skew viewing. The direction of skew viewing is set to 70°.

A light guide 13 is placed on the outer circumference of the main optical system 35 so that it can emit illumination light in the direction of a field. A light guide connector 4 with which an incident end of the light guide 13 is joined is formed in the proximal portion of the insertional part 34. Illumination light emanating from a light source unit is fed through the light guide connector 4. Even when the insertional part 34 serving as a main unit of the stereoscopic-vision endoscope is turned relative to the operation unit 3, illumination light can always be irradiated to a view range.

In the main optical system 35, an annular flare stop 36 for removing a flare spot from a prism or the like is joined with a parallel prism 35c between a 70° prism 35a and a meniscus convex lens 35b. FIGS. 21A and 21B show the structure of the flare stop 36. FIG. 21A is a front view showing the flare stop. FIG. 21B is a side sectional view. The flare stop 36 has an annular aperture so that a flare spot can be removed from a prism or the like in line with the zonal shift of the positions of right and left light paths in the front optical system in the insertional part 34.

FIG. 22 shows the layout of a rear optical system, a stop means, and imaging devices when the rotary unit 16 is viewed from ahead. Imaging devices 18 are placed on light paths, which are routed by two juxtapositional optical systems constituting a rotary optical system 15 serving as a rear optical system, behind the back optical system. Rays passing through apertures 20 of a stop means located in front of the rotary optical system 15 are projected on the imaging devices 18 by means of the rotary optical system 15. The rear optical system, stop means, and imaging devices are locked as a united body and can be rotated relative to the front optical system.

An operating assembly including the rotary unit 16 and operation unit 3 which are also employed in the first embodiment can be mounted in and joined with the insertional part 34 of this embodiment. As described previously, another front optical system permitting another direction of skew viewing can be combined with the rear optical system. By thus constituting various stereoscopic-vision endoscopes, directions of a field can be changed. When the front optical system in the first embodiment is exchanged for the one in the second embodiment, the direction of skew viewing can be changed from 30° to 70°.

When the front optical system is realized substantially with an afocal optical system, if the rear optical system is used in common and the front optical system is replaced with another one permitting another direction of a field, the spacing between the front and rear optical systems may be varied slightly due to mechanical backlash. Nevertheless, the focal point or magnitude of parallax can be held unchanged.

FIGS. 23 and 24A to 24C show the third embodiment of the present invention.

The third embodiment differs from the first embodiment, wherein the structure of a field conversion optical system in a front optical system is modified and one imaging device is used to receive right and left images.

In a stereoscopic-vision endoscope 40 of this embodiment, similarly to the one of the first embodiment, an insertional part 41 in which a front optical system is locked is coupled with an operation unit 42 that can be turned relative to the insertional part. The operation unit 42 is coupled with a rotary unit 43 including a rear optical system and lying in the insertional part 41. The operation unit 42 is rotatably attached to the insertional part 41 by fitting fixture projections 44a formed in the proximal portion of the insertional part 41 into fitting ditches 44b. The insertional part 41 cannot be separated from the operation unit 42.

In the insertional part 41, a main optical system 45 serving as a front optical system and having a single optical axis is incorporated. The main optical system 45 has prisms used for 30° skew viewing. Specifically, a rectangular prism 45a (roof prism) having a roof-like surface and a rectangular prism 45b having two reflection surfaces are placed with an air layer between them.

When the foregoing prism structure is discussed in comparison with the structure of the first embodiment using a 30° skew-view prism, since the length of a light path in a prism may be small, optical systems optimal to a compact endoscope can be realized.

Incident light entering the front optical system is reflected from the roof-like surface of the frontal roof prism 45a, and enters perpendicularly the incident surface of the back rectangular prism 45b. After being reflected from the bottom surface of the rectangular prism 45b, light is reflected totally by a surface adjoining the air layer, and enters a meniscus convex lens 45c.

Included in the rotary unit 43 are a rotary optical system 46 serving as a rear optical system and consisting of two juxtapositional optical systems, and one imaging device 47 for receiving right and left images formed by the rotary optical system 46 and photoelectrically transforming the images.

Figure 24A:
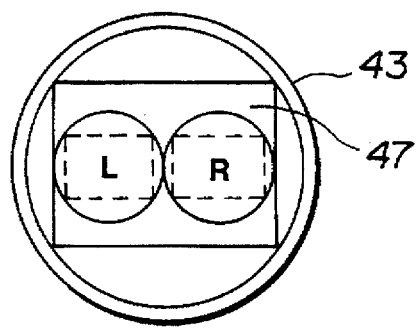
Figure 24B:
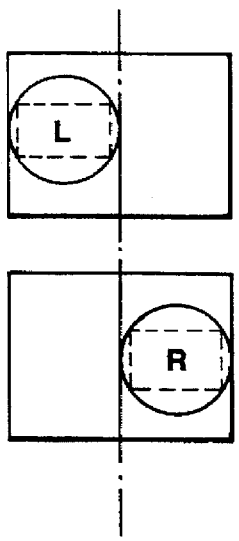
Figure 24C:
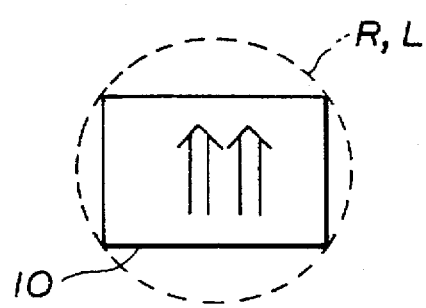

In this embodiment, the right and left images formed by the rear optical system are, as shown in FIG. 24A, projected on the right and left halves within an image area of an imaging surface of the imaging device 47. The right and left images are photoelectrically transformed by the imaging device 47, and electrically separated from one another. This result in the right and left independent images shown in FIG. 24B. Thereafter, enlargement of the images and alignment of the centers thereof are carried out. The right and left images which have been enlarged and of which centers have been aligned with each other are displayed as shown in FIG. 24C on a monitor 10 serving as a display unit. Right and left images causing parallax are thus produced, whereby stereoscopic visioning is enabled.

In the structure of this embodiment, one imaging device is used to receive right and left images. The location of the imaging device in an insertional part can be determined lightheartedly. Moreover, the number of signal lines linking the imaging device and a camera control unit may be small. The diameter of the insertional part can therefore be diminished.

In this embodiment, as long as a stop means lying in a rotary unit and having apertures and a back optical system composed of right and left juxtapositional optical systems are united with one another and can be rotated relative to a front optical system, an imaging device need not be rotated together with the rear optical system. As long as right and left images can be picked up by the imaging device, when the right and left images may be separated mutually and displayed in the same direction, stereoscopic visioning can be enabled.

Figure 25:
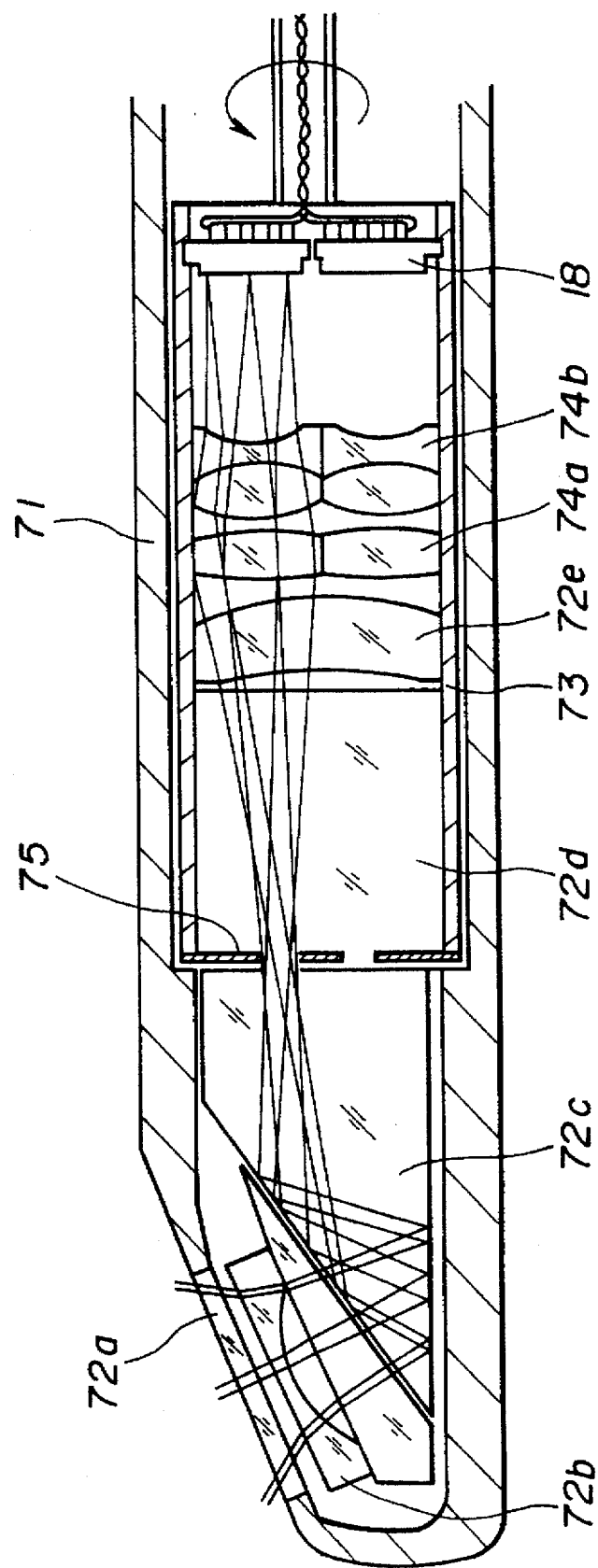
FIGS. 25 and 26 relate to the fourth embodiment of the present invention.
Figure 26:
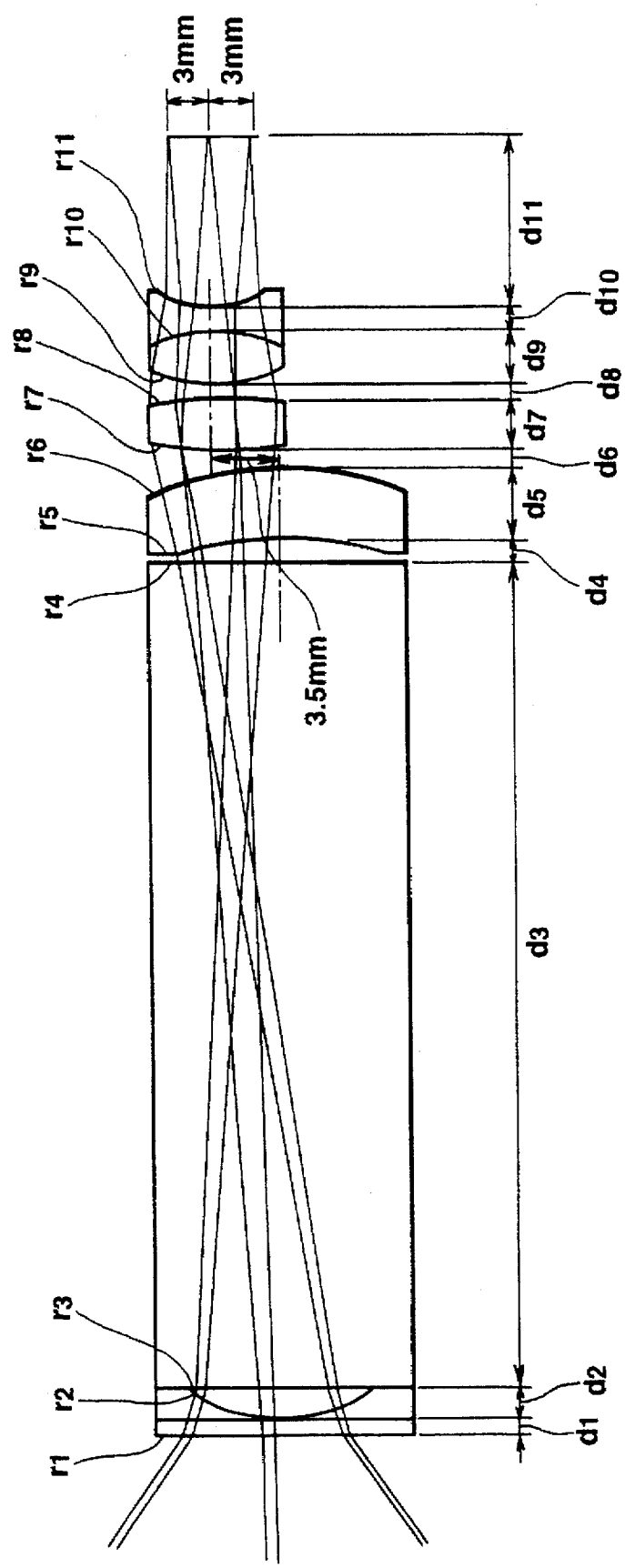

FIGS. 25 and 26 show the fourth embodiment of the present invention.

In the fourth embodiment, different component elements of front and rear optical systems are allotted to a stationary front assembly and a rotatable rear assembly respectively. The arrangement of optical systems in this embodiment can apply to the aforesaid embodiments. The other components are identical to those in the aforesaid embodiment. No mention will be made of the components.

In an insertional part 71 of a stereoscopic-vision endoscope of this embodiment, a cover glass 72a, plano-concave lens 72b, and 70° skew-view prism 72c, which are part of a front optical system, are arranged in that order from the distal end of the insertional part and constitute a front assembly locked in the insertional part.

A rotary unit 73 that can be turned relative to the insertional part and serves as a rear assembly is located behind the front assembly in the insertional part 71. The rotary unit 73 includes a plane parallel plate prism 72d and a meniscus convex lens 72e, which are part of the front optical system whose elements share the same axis, and a rear optical system composed of a pair of right and left optical systems being juxtaposed and having different optical axes. The rear optical system composed of the right and left juxtapositional optical systems consists of image formation optical systems each including a convex lens 74a and a meniscus lens 74b having a composition plane.

A stop 75 for providing right and left light beams that form right and left images causing parallax is interposed between the front and assemblies. The stop 75 is fixed to the front end of the rotary unit 73 and turned as part of the rear optical system.

The optical systems in this embodiment include a 70° skew-view prism 72c, thus enabling 70° skew viewing. FIG. 25 shows one of right and left paths of rays.

Practical design data concerning optical systems that are arranged as shown in FIG. 25 is listed below. FIG. 26 shows definitions of the design data items; that is, a radius of curvature r, a spacing d, a refractive index n, and an Abbe number v which are listed in Table 1. K denotes a surface number.

TABLE 1

| K | r | d | $n_d$ | $v_d$ |
|---|---|---|---|---|
| 1 | ∞ | 1 | 1.80518 | 25.4 |
| 2 | 10.1728 | 2 | 1 | |
| 3 | ∞ | 50 | 1.88300 | 40.8 |
| 4 | ∞ | 1 | 1 | |
| 5 | −38.80429 | 4.546056 | 1.723242 | 38.0 |
| 6 | −22.01229 | 1 | 1 | |
| 7 | 20.81875 | 3 | 1.83481 | 42.7 |
| 8 | −33.00288 | 1 | 1 | |
| 9 | 9.63813 | 3 | 1.72916 | 54.7 |
| 10 | −12.97095 | 1.582464 | 1.84666 | 23.8 |
| 11 | 7.86249 | 10 | | |

Herein, assuming that the parallel deviation of an optical axis of a system of lenses r7 to r11 from an optical axis of a system of lenses r1 to r6; that is, the eccentricity of the back optical system is 3.5 mm, that the focal length f' of the whole system of lenses is 4.5495, the back focal point fB thereof is 9.5698, the front focal point fF thereof is 8.1128, the f-number FNO thereof is 5.1, and the image height thereof is 3 mm, that the focal point f1 of a system of negative lenses (plano-concave lenses) in the front optical system is −12.634, and the focal length f2 of a system of positive lenses (meniscus convex lenses) in the front optical system is 63.134, the following expression is established:

$$|f1/f2|=|-12.634/63.134|\approx 0.20$$

Consequently, the distance between the optical axes of the systems of lenses is calculated as 3.5 mm×0.20=0.7 mm.

In this embodiment, front and back assemblies are separated from each other at a position between a concave lens and a convex lens included in a front optical system whose elements share the same optical axis. The diameter of a path of rays on an incident surface of the optical system whose elements share the same optical axis is not large. This is advantageous in that an insertional part into which optical systems are mounted can be designed to have a small diameter. Specifically, a stop for defining right and left light paths is interposed between the front concave lens and rear convex lens included in the front optical system. The stop, the convex lens included in the front optical system, a rear optical system composed of right and left juxtapositional optical systems, and an imaging device for picking up right and left images are stowed in a rotatable rear assembly, thus making it possible to correct of postures of images responsively to each rotation. This results in a more compact endoscope.

Figure 27:
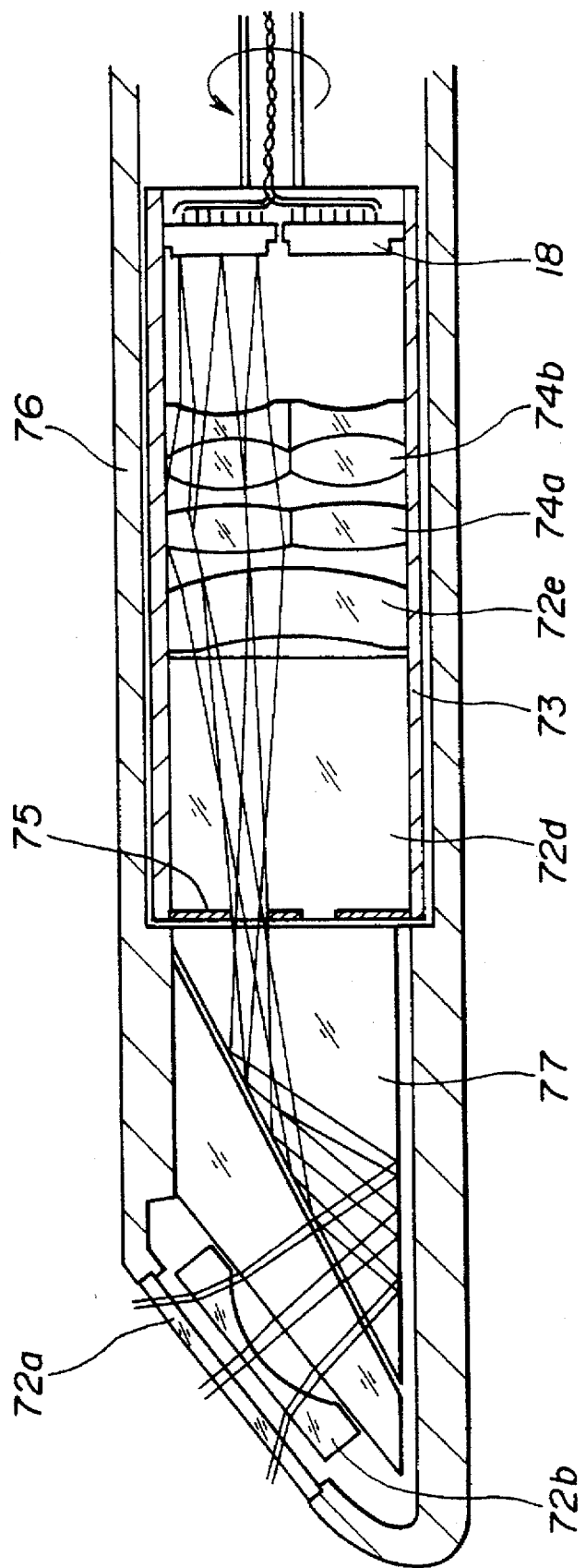
FIG. 27 is a longitudinal sectional view showing the structure of a major portion of a stereoscopic-vision endoscope in accordance with the fifth embodiment of the present invention.

FIG. 27 shows the fifth embodiment of the present invention.

The fifth embodiment is a variant of the fourth embodiment in terms of the arrangement of optical systems. The skew-view prism included in the front optical system of optical systems in the fourth embodiment is modified so that the direction of skew viewing will be 50°. In an insertional part 76 of the fifth embodiment, a 50° skew-view prism 77 is located behind a plano-concave lens 72b within a front optical system locked as a front assembly in the insertional part. The other components are identical to those of the fourth embodiment.

By thus modifying the structure of a field conversion optical system including a skew-view prism, the direction of skew viewing can be set to a desired angle for a stereoscopic-vision endoscope offering the same operation and advantages as the one of the fourth embodiment.

Figure 28:
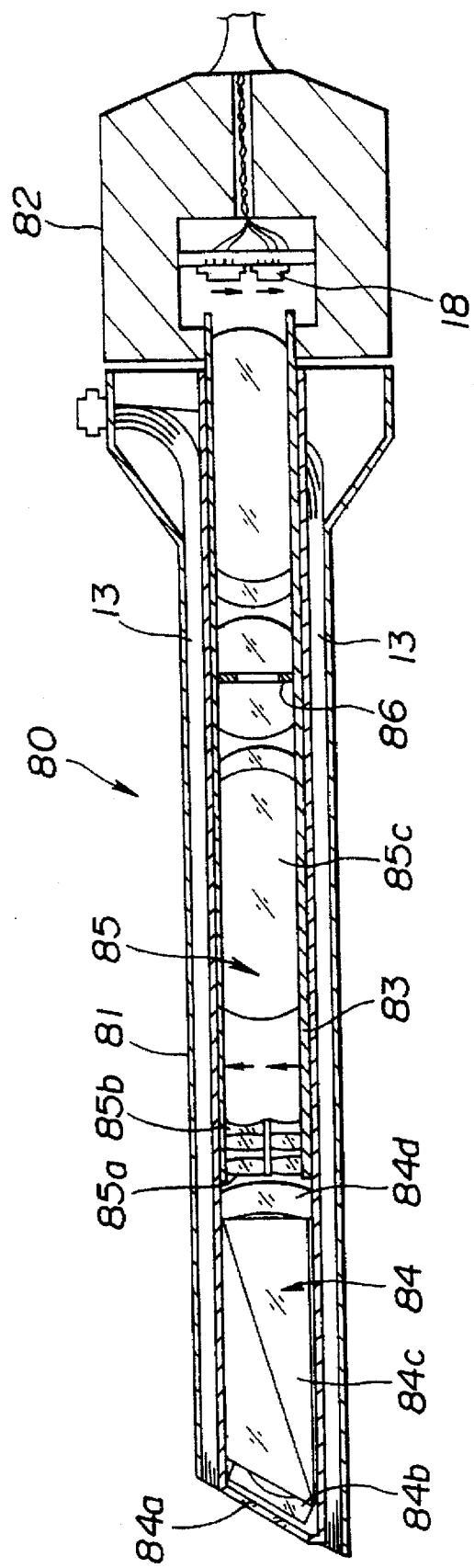
FIGS. 28 and 29 relate to the sixth embodiment of the present invention.
Figure 29:
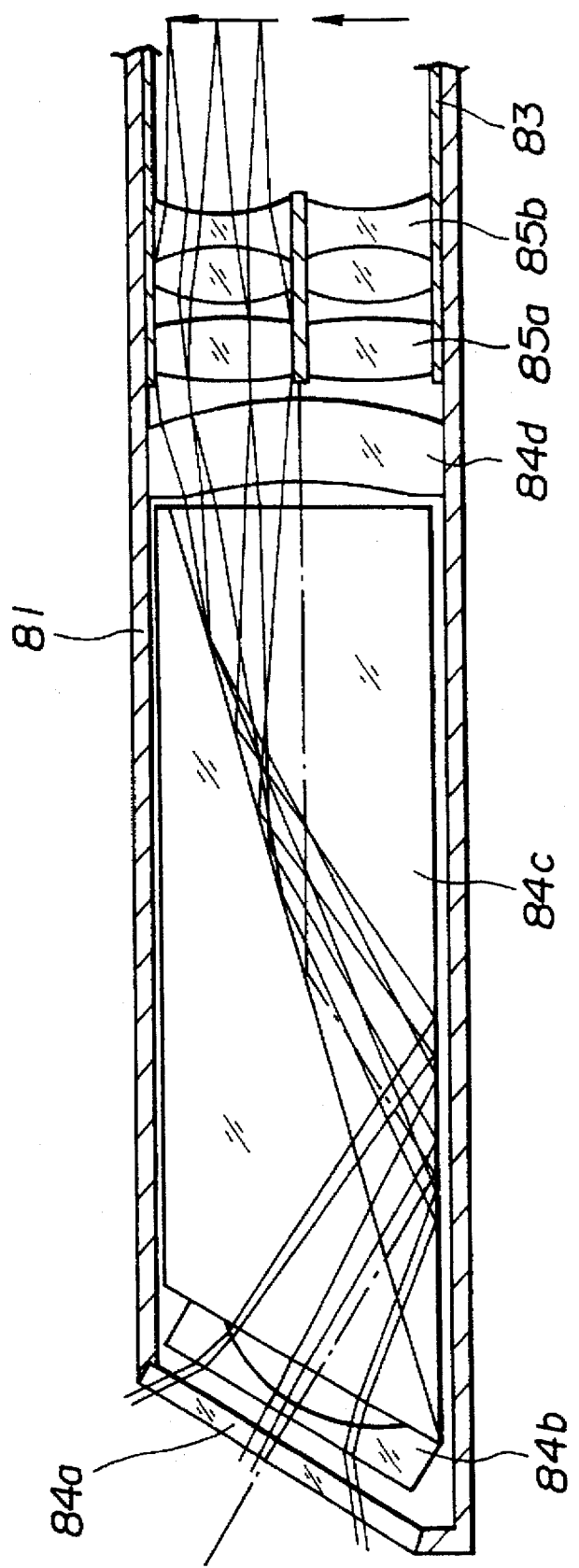

FIGS. 28 and 29 show the sixth embodiment of the present invention.

In the sixth embodiment, a relay optical system is used as a back optical system.

In a stereoscopic-vision endoscope 80 of this embodiment, similarly to the one of the first embodiment, an operation unit 82 that can be rotated relative to an insertional part is coupled to the insertional part 81 in which a front assembly including a front optical system is locked. A rotary unit 83 serving as a back assembly and including a rear optical system is joined with the operation unit 82, and mounted in the insertional part 81.

In the insertional part 81, a main optical system 84 having a single optical axis and serving as a front optical system is mounted. The main optical system 84 is composed of a cover glass 84a, a plano-concave lens 84b, a 30° skew-view prism 84c, and a meniscus convex lens 84d in that order from the distal end of the insertional part.

In the rotary unit 83, a rotary optical system 85 composed of a pair of optical systems being juxtaposed laterally, having different optical axes, and each having a convex lens 85a and a meniscus-jointed lens 85b, and a relay optical system 85c relaying images formed by the pair of optical systems and having a single optical axis is mounted as a rear optical system. Imaging devices 18 for picking up right and left images relayed by the relay optical system 85c are situated at the rear end of the rotary unit 83 within the operation unit 82.

In this embodiment, since a relay optical system is employed, a stop means for defining light beams to be routed through laterally-juxtaposed optical systems can be situated within the relay optical system but not in front of the right and left optical systems having different optical axes. In this embodiment, a stop 86 having one aperture is located in the middle of the relay optical system 85c. The relay optical system of the optical systems in this embodiment is realized with a tele-centric optical system having zero power. In addition, an exit pupil is supposed to be formed to infinity. When a light beam passing by the aperture in the relay optical system is traced back, right and left entrance pupils of the stop are formed within the skew-view prism 84c by the right and left juxtapositional optical systems.

It is impossible to create right and left apertures in a prism. When optical systems are arranged as those in this embodiment, entrance pupils can substantially be formed in the prism owing to a relay optical system. This results in the decreased diameter of a front optical system including a skew-view prism.

Since the relay optical system is used to relay right and left images, imaging devices can be situated within an operation unit at the proximal end of an endoscope other than in an elongated insertional part. As a result, a wide space is preserved for the imaging devices. Moreover, easy mounting of optical systems can be enabled without an increase in diameter of an endoscope.

In this embodiment, a stop having an aperture is situated in the middle of a relay optical system. When the length of the relay optical system is determined appropriately, the outer circumference of the relay optical system or the annular border of an interspace may be regarded as the outer circumference of an aperture of a stop. Eventually, the outer circumference of a lens may be regarded as that of an aperture of a stop.

FIG. 29 is an enlarged view showing the arrangement of optical systems of all the optical systems in this embodiment in the distal portion of an endoscope beyond the relay optical system. The optical systems have the same values of the radius of curvature r, spacing d, and refractive index n as those in the fourth embodiment. Since a prism permitting the direction of skew viewing of 30° is employed, the length of a light path in the prism is large. Consequently, the position of a stop is thought to be in the vicinity of a reflection surface of the prism. It becomes therefore difficult to position a stop. However, when the relay optical system is placed behind the optical systems, if a stop is situated within the relay optical system, entrance pupils of the stop are formed near the reflection surface of the prism. Thus, 30° skew viewing can be achieved with the diameter of the front optical system held small.

Figure 30:
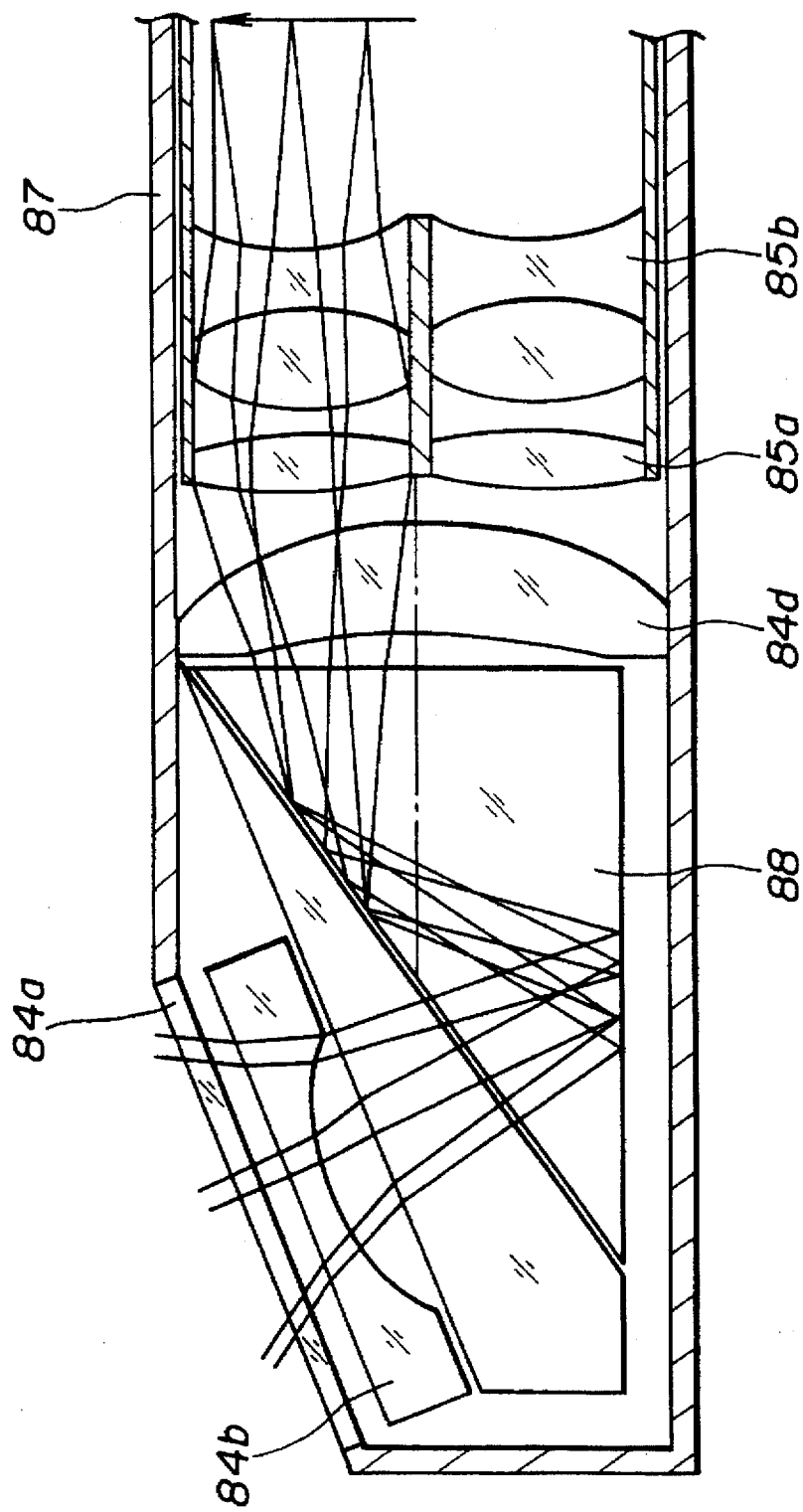
FIGS. 30 and 31 relate to the seventh embodiment of the present invention.
Figure 31:
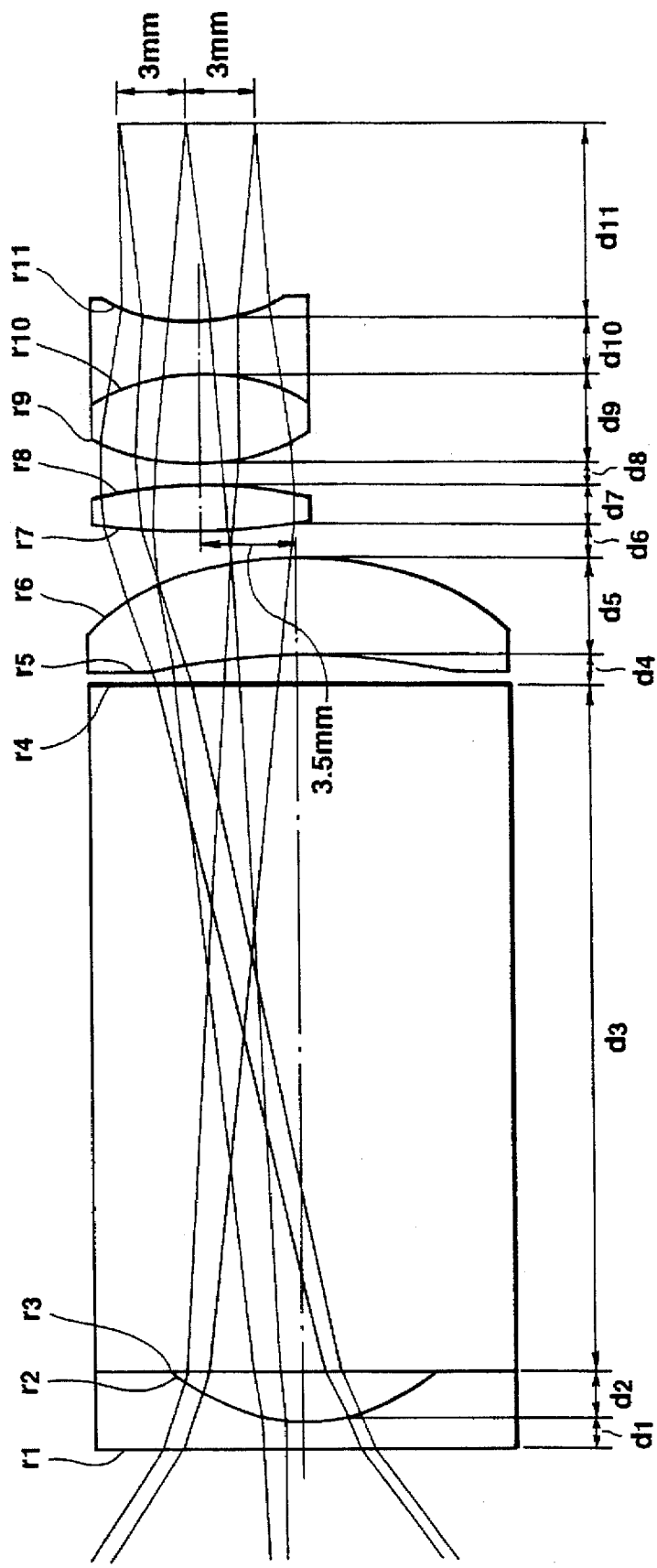
Figure 32:
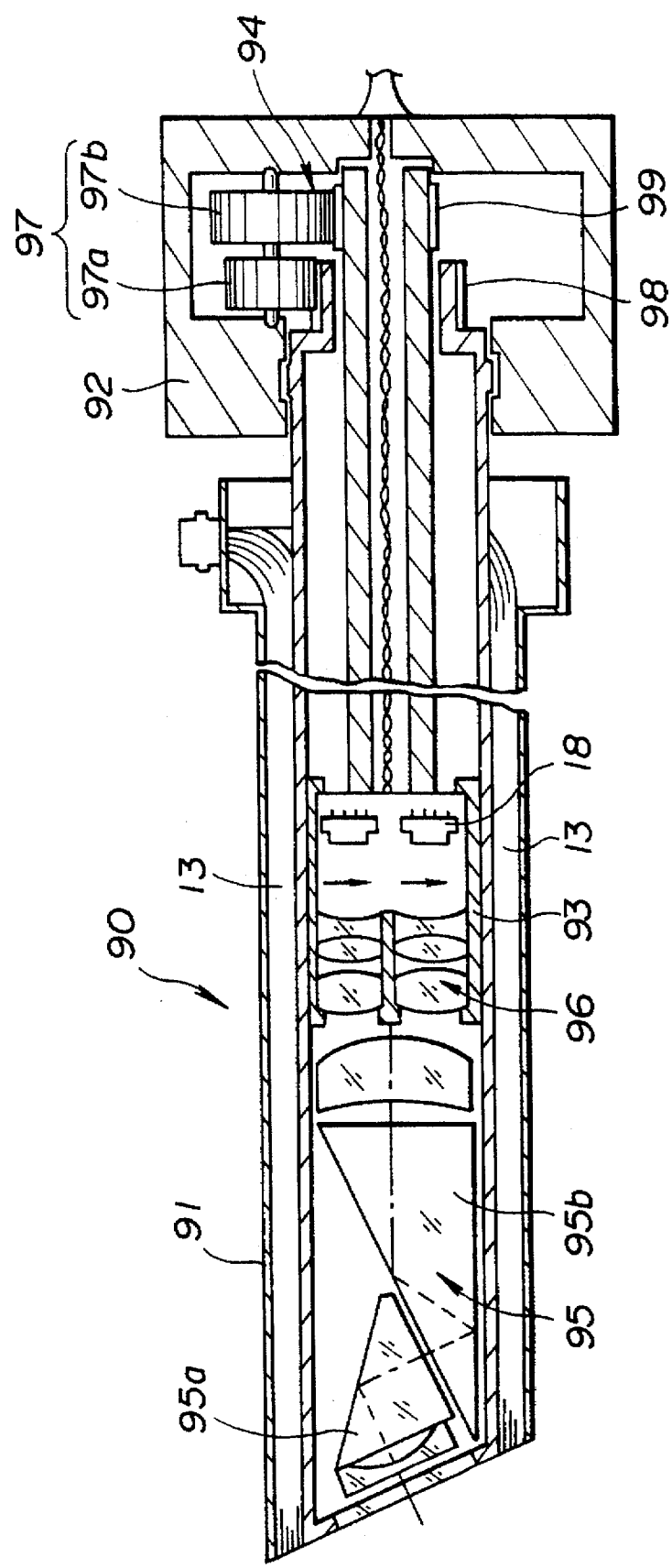
FIGS. 32 to 34, and 35A to 35C relate to the eighth embodiment of the present invention.

FIGS. 30 and 31 show the seventh embodiment of the present invention.

The seventh embodiment is a variant of the sixth embodiment in terms of the arrangement of optical systems. The skew-view prism in the front optical system of all the optical systems in the sixth embodiment is reformed to offer the direction of skew viewing of 70°. In an insertional part 87 of the seventh embodiment, a 70° skew-view prism 88 is placed behind a plano-concave lens 84b in a front optical system locked as a front assembly in the insertional part. The other components are identical to those of the fourth embodiment. A relay optical system that is not shown is placed behind optical systems 85a and 85b having different optical axes and serving as right and left optical systems constituting a rear optical system.

Practical design data for the optical systems arranged as shown in FIG. 30 is listed below. FIG. 31 illustrates definitions of the design data items; that is, a radius of curvature r, spacing d, refractive index n, and Abbe number which are listed in Table 2. K denotes a surface number.

TABLE 2

| K | r | d | $n_d$ | $v_d$ |
|---|---|---|---|---|
| 1 | ∞ | 1 | 1.882997 | 40.8 |
| 2 | 7.41591 | 2 | 1 | |
| 3 | ∞ | 25 | 1.846660 | 23.8 |
| 4 | ∞ | 1 | 1 | |
| 5 | −30.46895 | 3.628479 | 1.729157 | 54.7 |
| 6 | −13.06794 | 1 | 1 | |
| 7 | 29.28311 | 1.684222 | 1.834807 | 42.7 |
| 8 | −17.09735 | 0.852903 | 1 | |
| 9 | 9.65691 | 3 | 1.620041 | 36.3 |
| 10 | −10.10473 | 2 | 1.531717 | 48.9 |
| 11 | 9.08307 | 7 | 1 | |

Herein, assuming that the parallel deviation of an optical axis of a system of lenses r7 to r11 from an optical axis of a system of lenses r1 to r6 to; that is, the eccentricity of the back optical system is 3.5 mm, that the focal length f' of the whole system of lenses is 4.5746, the back focal point fB thereof is 6.5441, the front focal point fF thereof is 5.9032, the f-number FNO thereof is 4.7, and the image height thereof is 3 mm, that the focal point f1 of a system of negative lenses (plano-concave lenses) in the front optical system is −8.399, and that the focal length f2 of a system of positive lenses (meniscus convex lenses) in the front optical system is 28.845, the following expression is established:

$$|f1|/|f2|=|-8.399|/|28.545|=0.29$$

Consequently, the distance between optical axes of the systems of lenses is calculated as 3.5 mm×0.29=1.02 mm.

The arrangement of optical systems in this embodiment is analogous to that in the fourth embodiment. When the prism optical system to be placed in the distal portion of an endoscope is shortened, the endoscope will have a smaller-diameter and become more compact. When a relay optical system is situated similarly to the one in the sixth embodiment, imaging devices can be placed in the proximal portion of the endoscope. This means that the component elements of the stereoscopic-vision endoscope can be mounted readily.

FIGS. 32 to 34 and 35A to 35C show the eighth embodiment of the present invention.

In a stereoscopic-vision endoscope 90 of this embodiment, similarly to the one of the first embodiment, an operation unit 92 that can be rotated relative to an insertional part is coupled to the insertional part 91 in which a front optical system is locked. The insertional part 91 includes an imaging unit 93 having a rear optical system that can be rotated relative to the insertional part. The proximal ends of the insertional part 91 and imaging unit 93 are coupled to the operation unit 92 via a speed change gear mechanism 94.

The insertional part 91 includes a main optical system 95 serving as a front optical system, being arranged substantially similarly to the one of the third embodiment, and having a single optical axis. The imaging unit 93 consists of a rotary optical system 96 serving as a rear optical system and including two juxtapositional optical systems, and imaging devices 18 for receiving right and left images formed by the rotary optical system 96 and photoelectrically transforming the images.

In this embodiment, a skew-view prism permitting the direction of a field of 30° is included as a field conversion optical system in the front optical system. The prism is composed of two rectangular prisms 95a and 95b but is not a roof prism. The number of reflections made in the prism is set to three or an odd number. An image transmitted to the rear optical system is a reversed image. Moreover, when the insertional part 91 and imaging unit 93 are turned relative to each other in order to correct the postures of images, entrance pupils are also turned. This brings about the drawbacks below.

Figure 33:
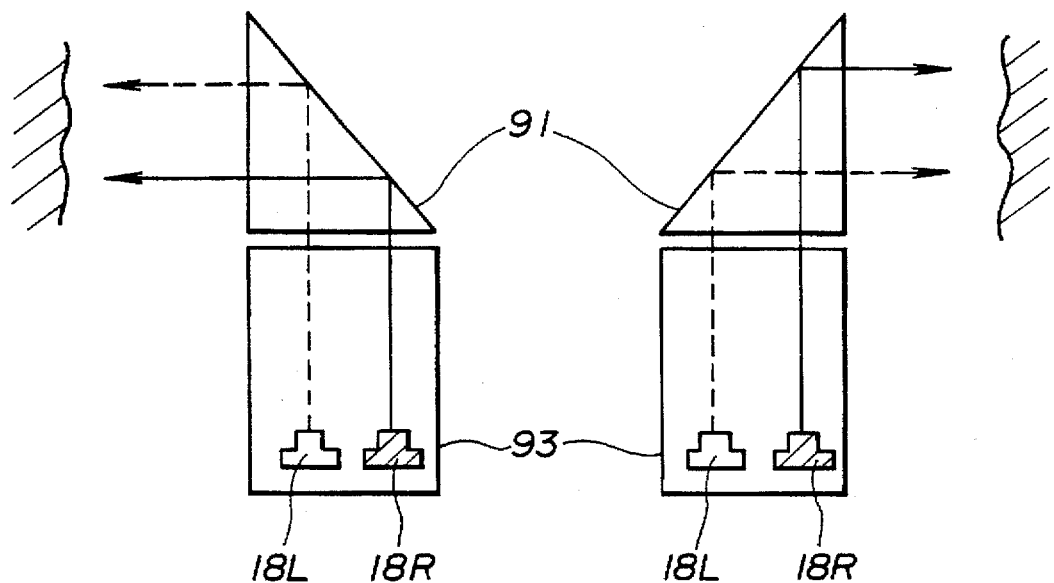

For example, as shown in FIG. 33, when the insertional part 91 is turned 180° relative to the imaging unit 93, images received by the right and left imaging devices 18R and 18L become inverses of right images that should be received thereby. Consequently, a sense of three-dimensionality is provided with left and right inverted.

As mentioned above, when a prism permitting an odd number of reflections is used to realize a compact design, images become reversed images. Moreover, the turn of entrance pupils results in an abnormal sense of three-dimensionality. In an effort to overcome this drawback, the speed change gear mechanism 94 is included in this embodiment for the purpose of adjusting the quantities of rotation by which the insertional part and imaging unit are turned.

Figure 34:
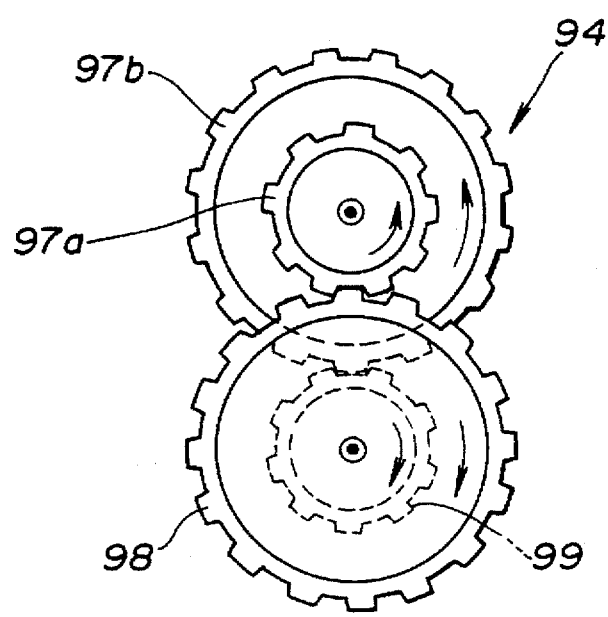

FIG. 34 shows the structure of the speed change gear mechanism 94. A double gear 97 made by joining a gear 97a with another gear 97b is supported by an axis inside the operation unit 92. Herein, the ratio of the number of teeth of the gear 97a to that of the gear 97b is 1:2. A gear 98 engaging with the gear 97a is formed on the outer circumference of the proximal portion of the insertional part 91. A gear 99 engaging with the gear 97b is formed on the outer circumference of the proximal portion of the imaging unit 93. Because of to this structure, the turn of the insertional part 91 is transmitted to the imaging unit 93 with the rotating speed changed at the ratio of 1:2. In other words, when the insertional part 91 is rotated by an angle of rotation θ, the imaging unit 93 is rotated by an angle 2θ.

Figure 35A:
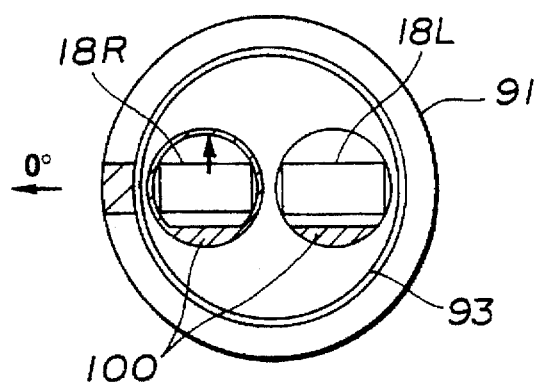
Figure 35B:
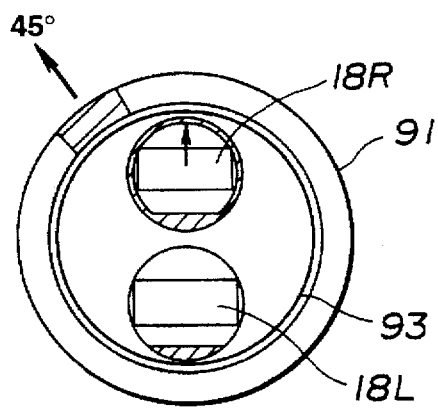
Figure 35C:
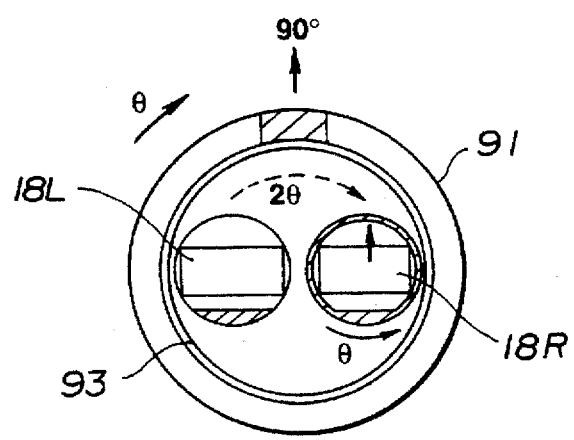

FIGS. 35A to 35C show quantities of rotation by which an imaging unit is rotated with the turn of an insertional part. When the insertional part 91 is rotated by 45° and 90° as shown in FIGS. 35B and 35C from an angular position (0°) shown in FIG. 35A, the back optical system, apertures, and imaging devices 18R and 18L in the imaging unit 93 are rotated by 90° and 180° respectively which are twice (2θ) as large as the angle of rotation θ of the insertional part 91. This makes it possible to project right and left entrance pupils on the right and left imaging devices through the right and left juxtapositional optical systems. Consequently, an abnormal sense of three-dimensionality resulting from the rotation of the entrance pupils can be avoided.

The foregoing measure is still insufficient. For correcting the turn of postures of images, the quantity of rotation by which the imaging devices 18 are to be turned must be corrected by the quantity of rotation by which the insertional part 91 is rotated. Specifically, when the insertional part 91 is rotated by the angle of rotation θ, the right and left imaging devices 18 must be rotated in an opposite direction by the angle θ about the optical axes thereof.

In this embodiment, as shown in FIGS. 35A to 35C, weights 100 are attached to the vertically lower sides (direction of gravity) of the imaging devices 18R and 18L so that the right and left imaging devices will be oriented in the same direction all the time. Consequently, when the insertional part 91 is rotated by the angle θ, the imaging unit 93 is rotated by the angle of 2θ. At this time, the imaging devices 18R and 18L are seen rotating by the angle θ in a direction opposite to the direction in which the insertional part and imaging unit are rotated.

As mentioned above, according to this embodiment, when a prism permitting an odd number of reflections is included in a field conversion optical system, an abnormal sense of three-dimensionality resulting from the turn of entrance pupils can be corrected properly. Similarly to the aforesaid embodiments, postures of images can be corrected responsively to the turn of an insertional part. This results in a stereoscopic-vision endoscope enabling correct stereoscopic visioning.

FIGS. 36A to 36C and 37A to 37C show the ninth embodiment of the present invention.

Figure 36A:
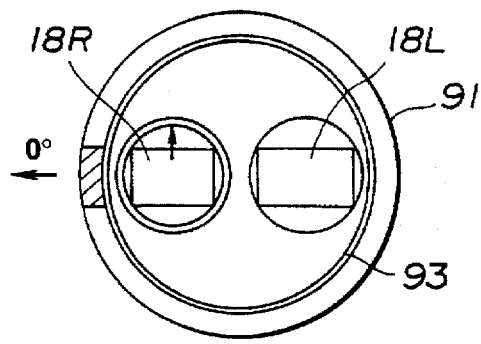
FIGS. 36A to 36C and 37A to 37C are explanatory diagrams concerning the operation of a stereoscopic-vision endoscope in accordance with the ninth embodiment of the present invention, and show the procedure of correcting the quantity of rotation, by which the imaging unit is rotated with the rotation of the insertional part, and the postures of images.
Figure 36B:
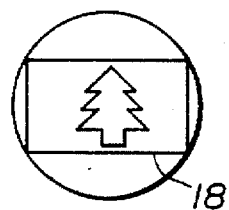
Figure 36C:
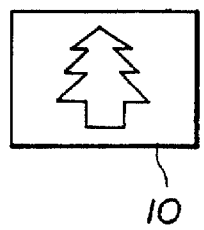

The ninth embodiment is a variant of the eighth embodiment, wherein postures of images are corrected by performing electrical processing but not by rotating imaging devices in an opposite direction. The configuration of a stereoscopic-vision endoscope is substantially identical to the one of the eighth embodiment. No mention will therefore be made of the configuration. FIGS. 36A and 36A show quantities of rotation by which an imaging unit is turned with the turn of an insertional part, and also show positions of imaging devices. FIGS. 36B and 37B show images projected on the imaging devices at the respective angular positions. FIGS. 36C and 37C show output images produced in the respective states.

Figure 37A:
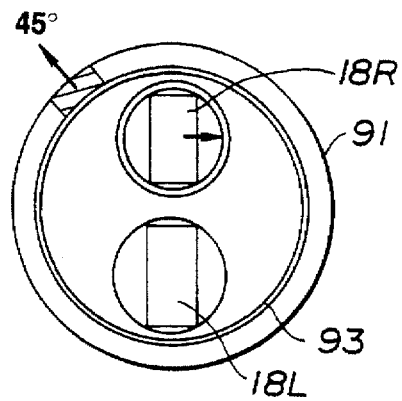
Figure 37B:
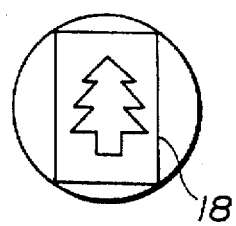
Figure 37C:
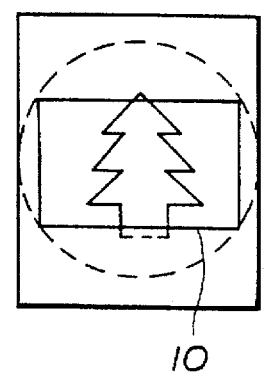

In this embodiment, as shown in FIGS. 36A and 37A, when the insertional part 91 is rotated by the angle θ (45°), the back optical system, apertures, and imaging devices 18R and 18L in the imaging unit 93 are, similarly to those in the eighth embodiment, rotated by the angle of rotation 2θ (90°) that is twice as large as the angle of rotation by which the insertional part 91 is turned. An abnormal sense of three-dimensionality resulting from the turn of the entrance pupils can therefore be avoided. At this time, the imaging devices 18R and 18L are not rotated by the angle θ in an opposite direction, but electrical processing is carried out for posture correction.

To be more specific, in this embodiment, as shown in FIG. 37A, when the insertional part 91 is turned, the angle of rotation by which the insertional part 91 is rotated from the angular position shown in FIG. 36A is detected. Thereafter, the images received by the imaging devices 18R and 18L, which are shown in FIG. 37B, are electrically enlarged or rotated by the angle θ (−θ) in an opposite direction. This results in the images shown in FIG. 37C. The images are displayed on the monitor 10 constituting a three-dimensional image display system. For detecting an angle of rotation by which the insertional part 91 is rotated, an encoder may be attached to the speed change gear mechanism 94 shown in FIG. 32. The output of the encoder is used to detect the angle of rotation. The electrical processing enables correction of image postures.

When projected images are turned in order to correct their postures, if images picked up by imaging devices having rectangular imaging areas are turned as they are, a blank is created in the perimeter of each image. For example, when the images are turned by 90°, a blank is created at each of the right and left edges of images. In this embodiment, projected images are enlarged before rotated by the angle θ in an opposite direction. Consequently, even when the images are turned, no blank appears in a display screen on the monitor.

Reversed images can be corrected readily by such a means that reads images placed in memory in a different direction and thus reverses the images electrically.

As described so far, according to the embodiments, a magnitude of parallax needed for providing a sufficient sense of three-dimensionality, which is unavailable in the pupil division technique, can be provided. Furthermore, image postures can be corrected responsively to a change in direction of view resulting from the turn of an insertional part. Not only for direct viewing but also for skew viewing, the directions of gravity in images appearing on a monitor can be corrected so that the direction of view will always be reflected on the images. This results in a stereoscopic-vision endoscope enabling correct stereoscopic-vision viewing.

In the present invention, it will be apparent that a wide range of different embodiments can be formed on the basis of the invention without departing from the spirit and scope of the invention. This invention will be limited to the appended claims but not restricted to any specific embodiments.

What is claimed is:

1. A stereoscopic-vision endoscope including a rigid insertional part, comprising:

an objective optical system comprising a front optical system having a single optical axis fixedly mounted within said insertional part including a field conversion optical system, and a rear optical system including optical systems that have a plurality of optical axes which receive a light beam from said front optical system so as to form images on said optical axes, and thus form a plurality of images, said front optical system and said rear optical system being relatively rotatable, said rear optical system being wholly contained within said insertional part.

2. The stereoscopic-vision endoscope according to claim 1, further comprising an imaging unit for picking up said plurality of images.

3. The stereoscopic-vision endoscope according to claim 2, wherein said imaging unit is formed with one imaging device,
wherein said imaging device picks up said plurality of images, and wherein a correcting means for electrically correcting postures of images is placed in a stage succeeding said imaging unit.

4. The stereoscopic-vision endoscope according to claim 1, wherein said front optical system comprises of a group of negative lenses, a field conversion optical system, and a group of positive lenses in that order from the end of said endoscope on the side of an object.

5. The stereoscopic-vision endoscope according to claim 4, wherein said front optical system is a substantially afocal optical system, wherein said rear optical system comprises two groups of positive lenses that are juxtaposed, and wherein whenever the focal length of said group of negative lenses in said front optical system is f1 and the focal length of said group of positive lenses in said front optical system if f2, the following condition is satisfied:

$$0.01 < |f1/f2| \leq 1.$$

6. The stereoscopic-vision endoscope according to claim 1, wherein a structure including a 30° skew-view roof prism is included as said field conversion optical system in said front optical system.

7. The stereoscopic-vision endoscope according to claim 1, wherein said field conversion optical system includes a prism that permits an odd number of reflections,
wherein said endoscope further comprises an optical system assembly including a main optical system that includes at least part of said front optical system, and said rear optical system that is rotatable relative to said main optical system,
wherein said optical system assembly is rotated in the same direction at a two-fold speed relative to said main optical system, and
wherein said imaging unit for receiving said plurality of images is rotated in an opposite direction at a speed ratio of 1:1 relative to said main optical system, and thus the postures of images are corrected.

8. The stereoscopic-vision endoscope according to claim 1, wherein an annular flare stop is situated in said front optical system.

9. A stereoscopic-vision endoscope including a rigid insertional part, comprising:

a front optical system fixedly mounted within said insertional part, said front optical system having a single optical axis and including a field conversion optical system;

a rear optical system including optical systems that have a plurality of optical axes which receive a light beam from said front optical system so as to form images on said optical axes, and thus form a plurality of images; and an imaging unit for picking up said plurality of images, said rear optical system and imaging unit being wholly contained within said insertional part and being rotatable as a united body relative to said front optical system.

10. A stereoscopic-vision endoscope, comprising:

an objective optical system comprising a front optical system having a single optical axis including a field conversion optical system, and a rear optical system including optical systems that have a plurality of optical axes which receive a light beam from said front optical system so as to form a plurality of images;

a relay optical system having a single optical axis for transmitting said plurality of images; and an imaging unit for picking up said plurality of images transmitted by said relay optical system, wherein said rear optical system, said relay optical system, and said imaging unit are rotatable as a united body relative to said front optical system in said objective optical system.

11. A stereoscopic-vision endoscope having an insertional part to be inserted into a space in an object to be observed for the purpose of stereoscopic viewing, comprising:

a front optical system lying in the distal portion of said insertional part and having a single optical axis;

a rear optical system including optical systems that lie succeedingly behind said front optical system which receive a light beam from said front optical system so as to form right and left images causing parallax, have different optical axes, and are juxtaposed; and a stop means lying in front of said juxtapositional optical systems that have different optical axes and having apertures for dividing said light beam emanating from said front optical system into right and left light beams, said front optical system, said stop means and said rear optical system being divided into a front assembly including only an optical system having the same optical axis and a rear assembly including said stop means and said optical systems having different optical axes; and said rear assembly being wholly contained within said insertional part and being rotatable as a united body relative to said front assembly.

12. A stereoscopic-vision endoscope having an insertional part to be inserted into a space an object to be observed for the purpose of stereoscopic viewing, comprising:

a front optical system lying in the distal portion of said insertional part and having a single optical axis;

a rear optical system contained wholly within said insertional part and being rotatable relative to said front optical system including optical systems that lie succeedingly behind said front optical system which receive a light beam from said front optical system so as to form fight and left images causing parallax, have different optical axes, and are juxtaposed; and a relay optical system for transmitting said right and left images, said relay optical system having a stop means for determining said parallax of said right and left images, said stop means forming entrance pupils in front of said juxtaposed optical systems.

13. The stereoscopic-vision endoscope according to claim 12, wherein said stop means has a single aperture, and said entrance pupils are formed by projecting said stop means by said juxtaposed optical systems, respectively.

14. A stereoscopic-vision endoscope having an insertional part to be inserted into a space in an object to be observed for the purpose of stereoscopic viewing, comprising:

a main optical system having a single optical axis mounted in and united with the distal portion of said insertional part; and a rear optical system including optical systems that receive a light beam from said main optical system so as to form a plurality of images causing parallax and that have different optical axes is stowed in an optical system assembly which is installed independently of said insertional part succeedingly behind said main optical system in said insertional part, wherein said optical system assembly is rotatable relative to said main optical system, wherein a relay optical system for transmitting said plurality of images is mounted in said optical system assembly together with said optical systems having different optical axes, wherein said optical system assembly is coupled to an insertional part installed independently of said insertional part, wherein an imaging unit for receiving said plurality of images is mounted in said optical system assembly inside said insertional part, and wherein said optical system assembly, imaging unit, and operation unit are rotatable as an operating assembly relative to a main unit of said endoscope including said insertional part.

15. The stereoscopic-vision endoscope according to claim 14, wherein said optical system assembly is coupled to an operation unit installed independently of said insertional part, wherein when said operation unit is rotated relative to said insertional part, said optical system assembly is rotated relative to said main optical system, and wherein an imaging unit for receiving said plurality of images is locked in said operation unit.

16. The stereoscopic-vision endoscope according to claim 12, wherein said optical system assembly includes an imaging unit for receiving said plurality of images.

\* \* \* \* \*